US012747206B2

(12) United States Patent
Nash

(10) Patent No.: US 12,747,206 B2
(45) Date of Patent: Sep. 29, 2026

(54) **BIOACTIVE PHYTOCHEMICALS IN *ZIZYPHUS* AND GUARANA**

(71) Applicant: Phytoquest Limited, Aberystwyth (GB)

(72) Inventor: Robert James Nash, Ystrad-Meurig (GB)

(73) Assignee: Phytoquest Limited, Aberystwyth (GB)

(*) Notice: Subject to any disclaimer, the term of this patent is extended or adjusted under 35 U.S.C. 154(b) by 1099 days.

(21) Appl. No.: 17/338,422

(22) Filed: Jun. 3, 2021

(65) Prior Publication Data

US 2021/0403424 A1 Dec. 30, 2021

Related U.S. Application Data

(63) Continuation of application No. PCT/GB2019/053422, filed on Dec. 4, 2019.

(30) Foreign Application Priority Data

Dec. 4, 2018 (GB) ..................................... 1819759

(51) Int. Cl.

| | |
|---|---|
| ***C07D 207/16*** | (2006.01) |
| ***A23L 33/105*** | (2016.01) |
| ***A61K 8/49*** | (2006.01) |
| ***A61K 36/725*** | (2006.01) |
| ***A61Q 19/00*** | (2006.01) |
| ***C07D 207/12*** | (2006.01) |

(52) U.S. Cl.

CPC .......... *C07D 207/16* (2013.01); *A23L 33/105* (2016.08); *A61K 8/4913* (2013.01); *A61K 36/725* (2013.01); *A61Q 19/00* (2013.01); *C07D 207/12* (2013.01); *A61K 2236/333* (2013.01); *A61K 2800/10* (2013.01)

(58) Field of Classification Search

CPC ... C07D 207/16; C07D 207/12; A23L 33/105; A61K 8/4913; A61K 36/725; A61K 2236/333; A61K 2800/10; A61K 36/77; A61Q 19/00; A61P 3/00; A61P 19/02

See application file for complete search history.

(56) References Cited

U.S. PATENT DOCUMENTS

2003/0059487 A1 3/2003 Niazi

FOREIGN PATENT DOCUMENTS

| | | | | | |
|---|---|---|---|---|---|
| JP | 2010-070531 | A | | 4/2010 | |
| WO | WO 2010/015816 | A2 | | 2/2010 | |
| WO | WO-2010029313 | A1 | * | 3/2010 | ............. A61P 31/00 |
| WO | WO 2010/049678 | A2 | | 5/2010 | |
| WO | WO 2014/089646 | A1 | | 6/2014 | |
| WO | WO 2016/191723 | A1 | | 12/2016 | |

OTHER PUBLICATIONS

De Aquino et al. (2016). The anti-inflammatory effects of N-methyl-(2S,4R)-trans-4-hydroxy-I-proline from Syderoxylon obtusifolium are related to its inhibition of TNF-alpha and inflammatory enzymes. Phytomedicine, 24, 14-23. (Year: 2016).*

Abdallah, E. M., Elsharkawy, E. R., & Ed-Dra, A. (2016). Biological activities of methanolic leaf extract of Ziziphus mauritiana. Bioscience Biotechnology Research Communications, 9(4), 605-614. (Year: 2016).*

PubChem, "N-methyl cis-4-hydroxymethyl-L-proline" CID 45109761, 9 pages. (Year: 2010).*

PubChem (CID 45109761) (Apr. 19, 2010) (Year: 2010).*

International Search Report and Written Opinion for Application No. PCT/GB2019/053422, mailed Feb. 28, 2020.

International Preliminary Report on Patentability for Application No. PCT/GB2019/053422, mailed Jun. 17, 2021.

Abdel-Zaher et al., Antidiabetic activity and toxicity of Zizyphus spina-christi leaves. J Ethnopharmacol. Oct. 3, 2005;101(1-3):129-38. doi: 10.1016/j.jep.2005.04.007.

* cited by examiner

*Primary Examiner* — James H Alstrum-Acevedo
*Assistant Examiner* — Pierre Paul Eleniste
(74) *Attorney, Agent, or Firm* — Wolf, Greenfield & Sacks, P.C.

(57) ABSTRACT

Described are compositions comprising selected isolated 4-hydroxymethyl-prolines, or pharmaceutically acceptable salts or derivatives thereof. Also described are novel 4-hydroxymethyl-N-methyl-prolines, together with processes for their preparation, compositions containing them, as well as their use as medicaments and pharmaceuticals. Also described are processes for producing a herbal medicine comprising the step of monitoring the quality of said herbal medicine by detecting the presence or absence or measuring the amount of one or more 4-hydroxymethyl-N-methyl-prolines in a sample of said herbal medicine.

8 Claims, 5 Drawing Sheets

BIOACTIVE PHYTOCHEMICALS IN *ZIZYPHUS* AND GUARANA

RELATED APPLICATIONS

This Application is a continuation of International Patent Application No. PCT/GB2019/053422, filed Dec. 4, 2019. Foreign priority benefits are claimed under 35 U.S.C. § 119(a)-(d) or 35 U.S.C. § 365(b) of British Application No. 1819759.0, filed Dec. 4, 2018. The entire contents of each of these applications are incorporated herein by reference.

FIELD OF THE INVENTION

The present invention relates to compositions comprising 4-hydroxymethyl-N-methyl-prolines and to their use in medicine, including the treatment of energy utilization disease, control of blood sugar, inflammation, bacterial infection, skin disorders, in vivo inhibition of sialidase activity, metabolic syndrome (including any disease or disorder associated therewith, for example central obesity, elevated levels of triglycerides and diabetes, including type 1 diabetes, type 2 diabetes and insulin resistance), to processes for isolating and purifying said compositions from various plant sources, together with various products, compounds, compositions, medical uses and methods based thereon.

The invention also relates to methods for monitoring the quality of *Zizyphus* and Guarana herbal medicines, supplements and extracts, to processes for producing herbal medicines based on *Zizyphus* and Guarana extracts as well as to herbal food additives, foods and beverages obtainable by such processes.

BACKGROUND OF THE INVENTION

*Zizyphus* spp.

*Zizyphus* is a genus, with many species, of spiny shrubs and small trees in the buckthorn family, Rhamnaceae. They are distributed in tropical and subtropical regions throughout the world. The fruit is an edible drupe, yellow-brown, red, or black, often very sweet and sugary, reminiscent of a date in texture and flavour. Well-known species include *Z. jujuba, Z. spina-christi, Z. lotus, Z. maurtiana* and *Z. joazeiro.*

*Zizyphus jujuba* has a fruit, jujube, which is also known as Chinese date and which is used in traditional Chinese medicine. It is believed to nourish the heart and calm the spirit, and is used to treat irritability, insomnia and heart palpitations. Other traditional uses of *Zizyphus* species include the treatment of diseases such as digestive disorders, liver complaints, urinary disorders, diabetes, skin infections and fever. It is used as a treatment for eczema (Khiljee at al., 2011, Journal of Pakistan Association of Dermatologists 21, 112).

*Zizyphus spina-christi* is a wild tree that will grow in desert areas and that is plentiful throughout the Middle East. Its leaves are a rich source of protein for desert animals and the small brown fruits are eaten by the local people. All parts of the plant are traditionally used by local people to help maintain their health. Antibacterial, antifungal, antioxidant and anti-inflammatory properties have been attributed to the plant, and an extract of the leaves is used for the treatment of wounds and skin diseases. Infusions of the dried leaves are used as a skin cleanser and for hair treatment. Its root bark is also used in folk medicine as a remedy against pain.

Studies on the chemical constituents of the plant are well-documented (Abdel-Zaher, A. et al., 2005, J. Ethnopharmacol. 101,129). A number of peptide and cyclopeptide alkaloids, flavonoids, triterpenoid saponin glycosides and betulinic acid have been identified in varying amounts in various species of the genus (Han, B., et al., 1990, Phytochemistry 29, 3315; Solati, J. & Soleimani, N., 2010, Acta Diabetol., 47, 219).

Recently the composition, antioxidant activities, and hepatoprotective effects of water extracts of *Zizyphus jujuba* have been evaluated (Liu. N. et al., 2017, RSC Adv. 7, 6511). A more detailed analysis of *Z. jujuba* fruit has been carried out by Villanueva, J. R. & Villanueva, L. R. (2017. Phytotherapy Research, 31, 347).

The literature contains many scientific studies regarding the use of *Z. spina-christi* for the treatment of diabetes (e.g. Nesseem, D., et al., 2009, Pharmazie 64, 104). Extracts of the plant are reported to possess antihyperglycemic activity (e.g. Abdel-Zaher. A. et al., 2005, J. Ethnopharmacol. 101, 129). Methanol extracts of *Z. spina christi* and *Z. jujuba* roots used for the treatment of alloxan diabetic rats were claimed to have beneficial effects on diabetic rats with reduced hyperglycemia, hyperlipdemia and lipid peroxides (Hussein, H., et al., 2006, International Journal of Pharmacology 2, 563). Hussein et al. attribute the activity to strong anti-oxidant activity which is not a property of the compounds of the Invention.

Tanira, M., et al., 1988, International Journal of Pharmacology 2, 563) tested an ethanolic extract of the leaves of *Z. spina-christi* in mice and showed anti-inflammatory and moderate antipyretic activity. Motamedi, H. et al., (2009, Asian Journal of Plant Sciences 8, 187) report ethanolic and methanoic leaf extracts of *Z. spina-christi* as potential sources of new anti-microbial compounds but it is now clear that common fatty acids (hexadecanoic acid) of most plants contain strong anti-microbial activity. Motamedi et al. do not identify the 4-hydroxymethyl-N-methyl-prolines as potential active components nor suggest uses of the fruits.

Borgi, W. et al., (2007, Fitoterapia 78, 16) reported aqueous and methanolic extracts of *Z. lotus* root barks showed significant anti-inflammatory effect in the acute phase of the inflammation process but related to anti-oxidant effects. U.S. Pat. No. 5,849,302 and EP 0815 842 A2 entitled 'Extracts of *Z. spina-christi* for cosmetics and psoriasis' describe leaf extracts using a 10% aqueous extract of *Z. spina-christi* leaves, which showed an anti-inflammatory activity on UV-irradiated skin in healthy volunteers with a reduction of 17.5% of redness across all subjects.

However, none of the 4-hydroxymethyl-N-methyl-prolines described herein (nor any similar compounds) have been reported from *Zizyphus* and these compounds have not been suggested to be involved in any of the bioactivity studies. Rather, interest in this regard has been focused on structurally unrelated triterpenes, anti-oxidants and peptides.

Guarana

The 4-hydroxymethyl-N-methyl-L-prolines as described here as bioactive phytochemicals present in *Zizyphus* species are not reported by other groups have surprisingly now also been discovered in fruits of Guarana, *Paullinia cupana* (family Sapindaceae, not closely related to *Zizyphus*).

*Paullinia cupana* is native to the Amazon basin and especially common in Brazil. Guarana is best known for the seeds from its fruit, which are about the size of a coffee bean and used as a dietary supplement, most noted for high caffeine content (its seeds contain about twice the concentration of caffeine found in coffee seeds: caffeine is present at levels of about 2%-4.5% in Guarana seeds compared to 1%-2% for coffee seeds—Bempong, D. K., et al., 1993, Int. J. Pharmacog. 31, 175).

The first report about the use of Guarana as a beverage occurred in 1669 when, during the Jesuit expedition to the Amazon, the missionary João Felipe Bettendorf observed that the Sateré-Mawé Indians consumed a stimulating beverage that had diuretic properties and therapeutic effects against headache, fever and cramps. Guarana is currently used in sweetened or carbonated soft drinks and energy shots, an ingredient of herbal teas or contained in capsules. *Zizyphus* contains no caffeine.

The therapeutic properties of Guarana as a stimulant, tonic and aphrodisiac have become known worldwide since the first reports of its indigenous use. The seeds are the commercially useful part of the plant because of their content of caffeine (1,3,7-trimethylxanthine), to which the stimulant property of Guarana is attributed (Kofink, M., et al., 2007, European Food Research and Technology 225, 589; Campos, M. P. D. et al., 2011, Journal of Alternative and Complementary Medicine 17, 505).

In addition to the psychoactive effects, the use of Guarana for metabolic disorders has been widely studied because it seems to possess functional properties similar to green tea, which is also rich in catechins. Studies have shown that Guarana positively affects lipid metabolism, increases basal energy and weight loss and may be useful for obesity treatments (e.g. Opala, T., et al., 2006, European Journal of Medical Research 11, 343).

Other studies have, however, shown no effect on body weight of a formula containing Guarana (Sale, C., et al., 2006, Int. J. Obes. (Lond.), 30, 764) and this highlights the need to produce quality-controlled extracts measuring compounds shown to have specific activities in vitro or in vivo (such as shown for the first time by the present inventors for the 4-hydroxymethyl-N-methyl-L-prolines).

The 4-hydroxymethyl-N-methyl-prolines described herein (and any similar compounds) have not been reported from Guarana and these compounds have not been suggested to be bioactive phytochemicals. Rather, interest in this regard has been focused on structurally unrelated chemicals, Including methylxanthines, catechins, methylbenzenes, cyclic monoterpenes, sesquiterpenes, oleic acid, paullinic acid and methoxyphenyl propene (Avato, P., et al., 2003, Lipids 38, 773-780).

Herbal Food Additives and Remedies

There is presently great interest in the use of herbal remedies and supplements and a growing acceptance from food manufacturers, healthcare companies and the medical profession that herbal products have value and can complement established formulations and treatments. Herbal food additives and supplements are now widely used.

However, quality control of herbal food additives is difficult due to the complex nature and inherent non-uniformity of plant materials. The materials used in herbal and plant-based food additives are usually whole plants or parts or extracts thereof. Since plant materials contain many different chemical components the materials are complex mixtures. This makes it very difficult to standardize and control the quality of the materials. Moreover, many herbal food additives are mixtures of two or more plant-based components and are therefore mixtures of mixtures, so introducing a further level of complexity. Furthermore, the recipes and methods of manufacture used are often not uniform and may remain undisclosed. These factors make it very difficult to ensure that two samples of a given product, obtained from disparate sources and ostensibly Identical, do in fact contain the same mixture of ingredients. This problem, which leads to difficulties in controlling the quality of such materials, has limited the use of certain herbal extracts even amongst herbal practitioners.

Other problems arise from the fact that the plants used in the practice of herbal food additive are frequently unavailable locally and therefore need to be obtained from sources which are remote from the end user. However, the supply of such plants from remote locations can be erratic and inaccurate, particularity because no detailed monographs including identity and quality standards exist for many such plants. The complex mixture of Ingredients found in medicinal plants varies widely in type and concentration depending on many factors including the botanical source, the location where the plant is grown, what other plants or microorganisms are growing near it, the time of year when the plant is harvested, the conditions under which the material is stored and processed and the extraction procedure used.

There is therefore a need for sensitive processes which can profile herbal products and so establish a standard specification for a medicinal plant material which can be related to activity, so permitting quality control in the production of herbal food additives and ideally quantifying the components known or likely to be active.

The present inventor has now discovered that the botanical distribution of certain 4-hydroxymethyl-N-methyl-prolines correlates with *Zizyphus* and Guarana plants used for the treatment of various diseases. This discovery is of great commercial and medical significance, and permits for the first time the synthesis and/or isolation of a new family of therapeutically-active 4-hydroxymethyl-N-methyl-prolines, the production of improved herbal medicines meeting a standard specification and a range of therapeutic treatments based thereon.

SUMMARY OF THE INVENTION

The present invention is based, at least in part, on the surprising discovery that the botanical distribution of certain 4-hydroxymethyl-N-methyl-prolines correlates with medicinal plants used for the treatment of various diseases. Thus, for the first time a family of 4-hydroxymethyl-N-methyl-prolines has been identified as important bioactive principles in established herbal medicines.

Thus, according to the invention there is provided a composition comprising an isolated 4-hydroxymethyl-proline selected from:

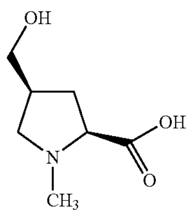

1

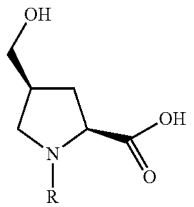

1b

-continued
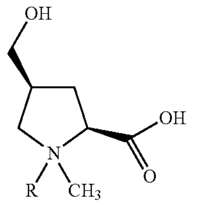
1c
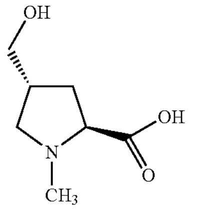
2
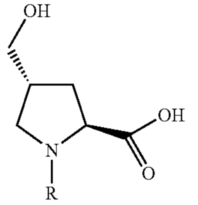
2b
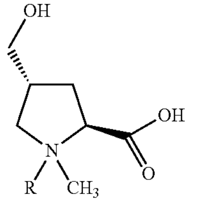
2c
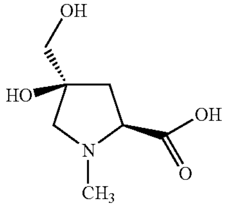
3
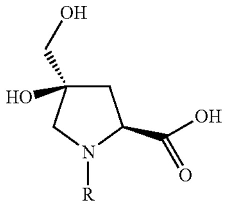
3b
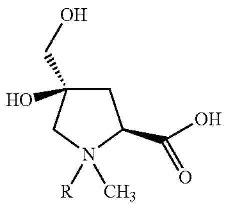
3c
-continued
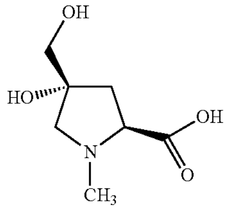
4
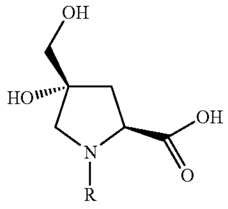
4b
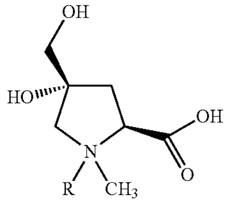
4c
or a pharmaceutically acceptable salt or derivative thereof, in which R represents optionally substituted C1-6 alkyl, C1-6 alkenyl or C1-6 alkynyl.
In preferred embodiments, the 4-hydroxymethyl-proline is selected from:
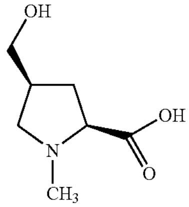
1
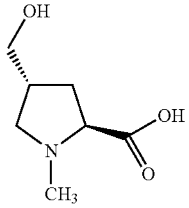
2
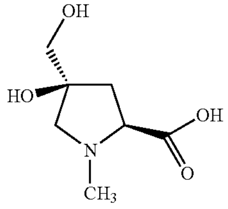
3

-continued

4

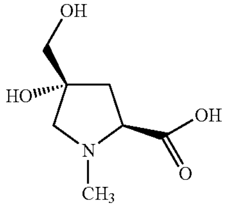

or a pharmaceutically acceptable salt or derivative thereof.

Other embodiments of the invention are defined in the claims appended hereto.

Certain 4-hydroxymethyl-N-methyl-prolines described herein are novel. According to the invention, we also provide those novel 4-hydroxymethyl-N-methyl-prolines as products per se, together with processes for their preparation, compositions containing them, as well as their use as medicaments and pharmaceuticals. To the extent that some of the 4-hydroxymethyl-N-methyl-prolines described herein are known, as such, they have not been recognized as bioactive and are therefore claimed as pharmaceuticals per se.

Herbal Quality Monitoring Aspects of the Invention

According to another aspect of the present invention there is provided a process for producing a herbal medicine comprising the step of monitoring the quality of said herbal medicine by detecting the presence or absence or measuring the amount of one or more 4-hydroxymethyl-N-methyl-prolines in a sample of said herbal medicine.

In another aspect, the invention provides a method for monitoring the quality of a herbal medicine comprising the steps of: (a) providing a sample of the herbal medicine; and (b) detecting the presence or absence or measuring the amount of one or more 4-hydroxymethyl-N-methyl-prolines in a sample of said herbal medicine.

In this context, the term quality is used to define the overall fitness of the herbal medicine for its intended use, and may include for example the presence or absence of one or more 4-hydroxymethyl-N-methyl-prolines in a sample of said herbal medicine (at an appropriate concentration) which indicates the use of a particular source, condition, purity and an acceptable or unacceptable degree of contamination with undesirable supplements and/or contaminants.

In a further aspect, the invention provides a process for producing a supplemented foodstuff or beverage comprising the steps of:

(a) providing plant parts of *Zizyphus* spp. and/or *Paullinia cupana;*
(b) monitoring the quality of said plant parts according to the method of the invention; and
(c) adding the plant parts (or one or more fractions thereof) to a foodstuff or beverage to produce said supplemented foodstuff or beverage.

This aspect of the invention finds broad utility in the production of any supplemented foodstuff or beverage and any foodstuff or beverage may be used, including chilled foods and beverages, hot foods and beverages, sweetened foods and beverages, carbonated beverages, alcoholic beverages and non-alcoholic beverages.

The processes and methods of the invention preferably further comprise the step of detecting the presence or absence or measuring the amount of one or more 4-hydroxymethyl-N-methyl-prolines in said sample of herbal food additive.

In embodiments where the presence of one or more 4-hydroxymethyl-N-methyl-prolines are detected according to the invention, preferred are processes in which one or more 4-hydroxymethyl-proline selected from:

1

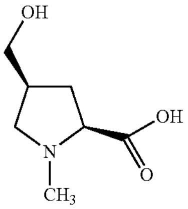

1b

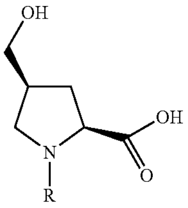

1c

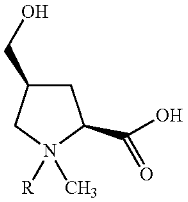

2

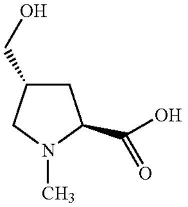

2b

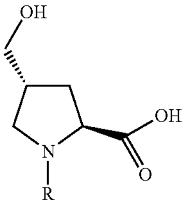

2c

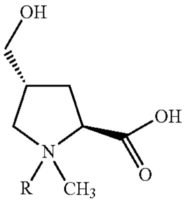

3

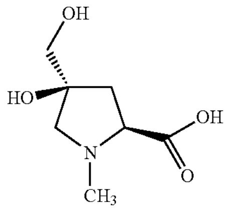

-continued

3b

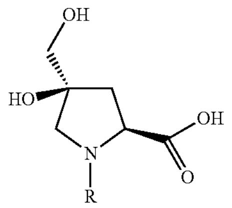

3c

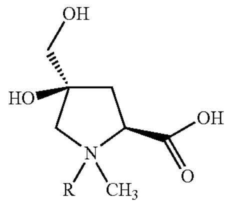

4

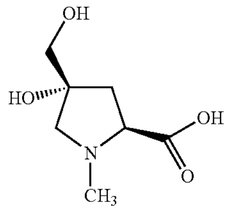

4b

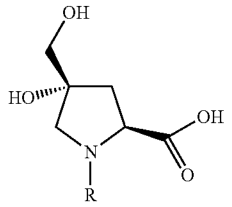

4c

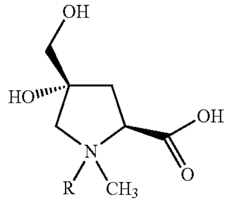

in which R represents optionally substituted C1-6 alkyl, C1-6 alkenyl or C1-6 alkynyl, are assayed, detected or monitored.

In other embodiments where the presence of one or more 4-hydroxymethyl-N-methyl-prolines are detected according to the invention, particularly preferred are processes in which one or more 4-hydroxymethyl-proline selected from:

1

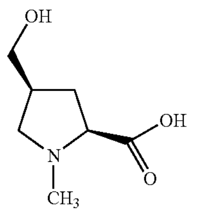

-continued

2

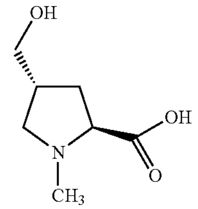

3

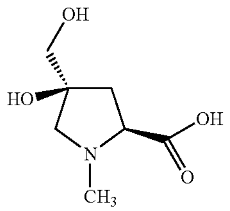

4

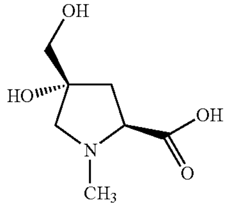

are assayed, detected or monitored.

The invention also contemplates a herbal medicine obtainable by the methods and processes of the invention.

Following incubation at 37 °C (5% $CO_2$, 100% humidity) plasma was collected from blood by centrifugation and the levels of TNF-α in plasma samples were measured by ELISA. Values represent the means + s.d. of n=3.

Figure 2:
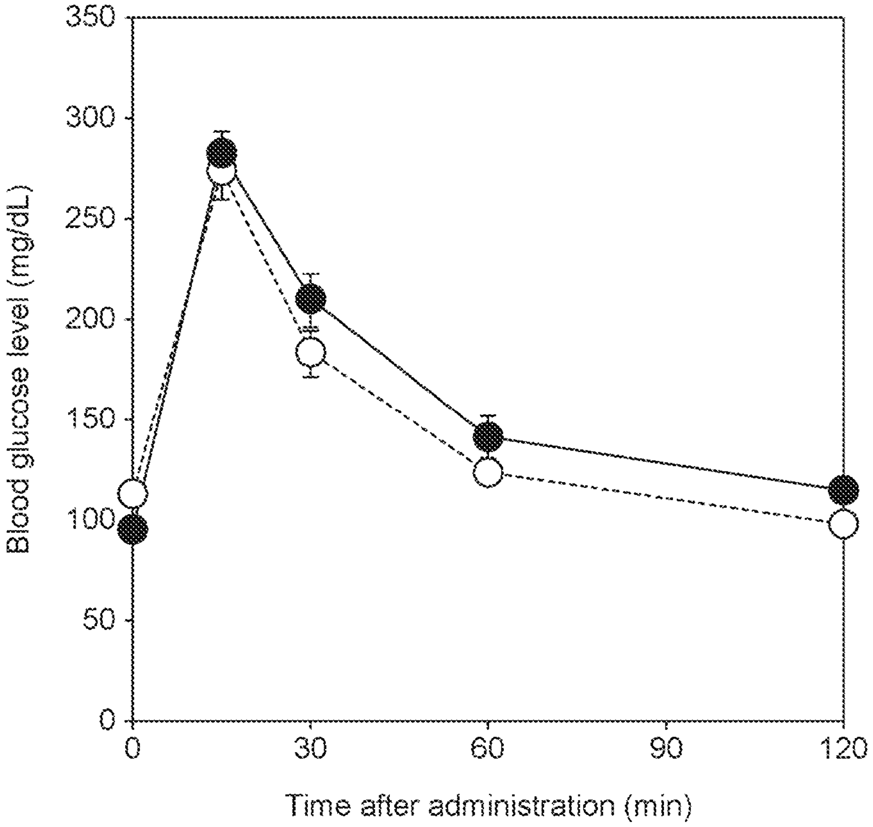

FIG. 2 shows the effects of Zizyphus extract on blood glucose levels. Blood glucose concentrations of male C57BL/6J mouse after an oral load with 2.5 g/kg body weight glucose with Zizyphus extract (each 1000 mg/kg body weight) extracts (open circle). The control group was loaded with saline (closed circle). Each value represents the mean + SEM (n=5).

Figure 3:
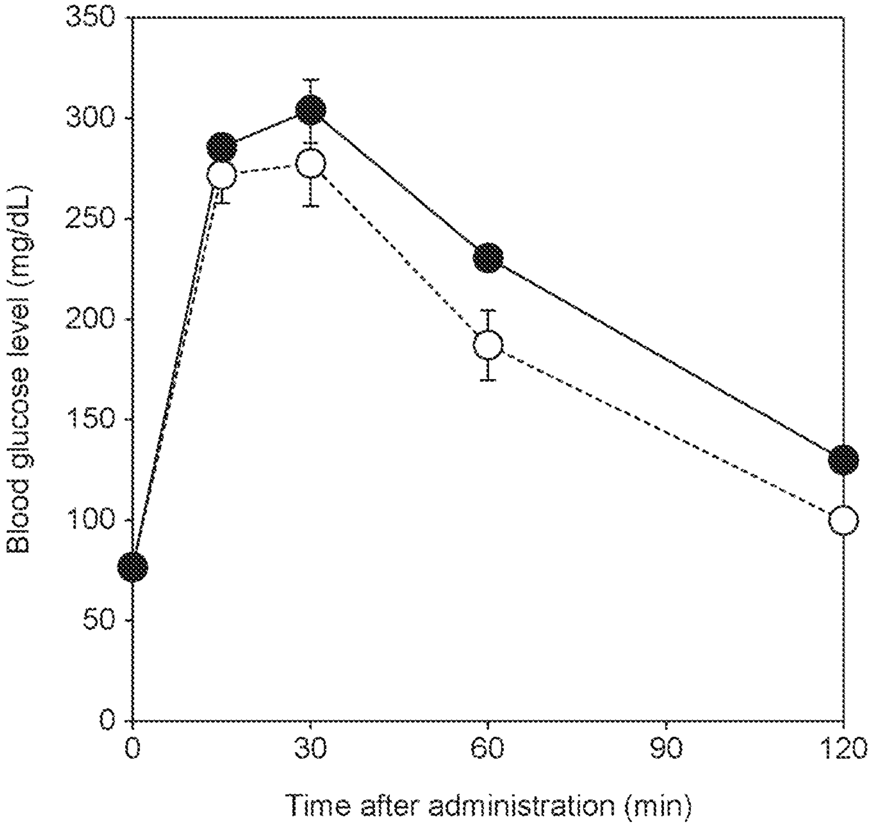

FIG. 3 shows the effects of Zizyphus extract on blood glucose levels. Blood glucose concentrations of male C57BL/6J mouse after an oral load with 2.5 g/kg body weight glucose with Zizyphus extract (each 500 mg/kg body weight) extracts (open circle). The control group was loaded with saline (closed circle). Each value represents the mean + SEM (n=5).

Figure 4:
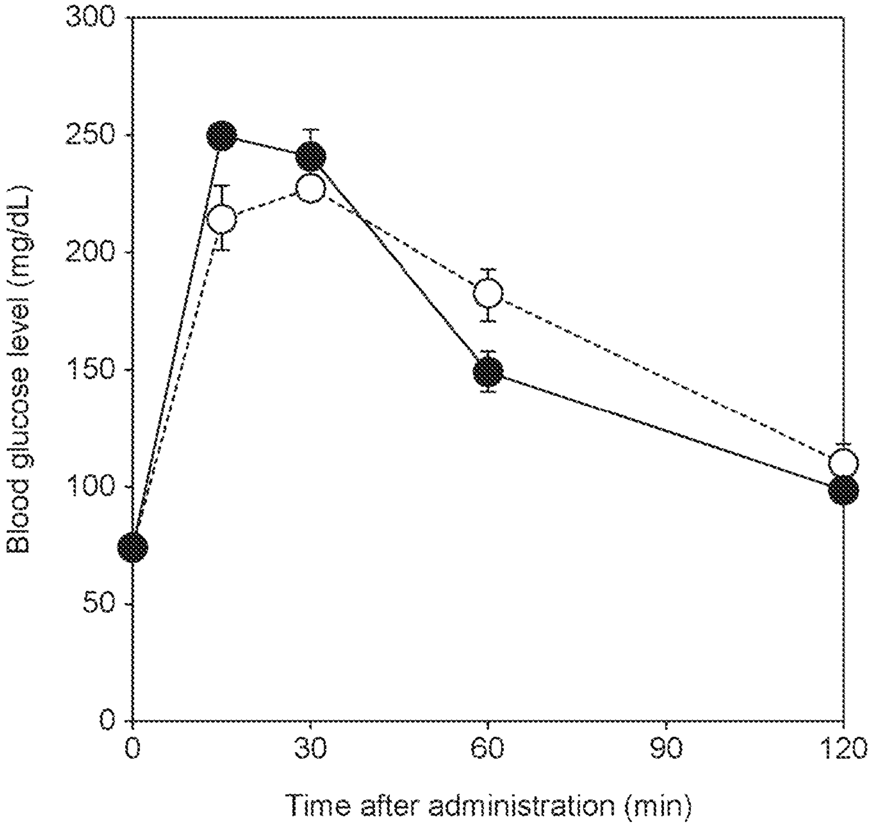

FIG. 4 shows the effects of Zizyphus extract on blood glucose levels. Blood glucose concentrations of male C57BL/6J mouse after an oral load with 2.5 g/kg body weight sucrose with Zizyphus extract (each 1000 mg/kg body weight) extracts (open circle). The control group was loaded with saline (closed circle). Each value represents the mean + SEM (n=5).

Figure 5:
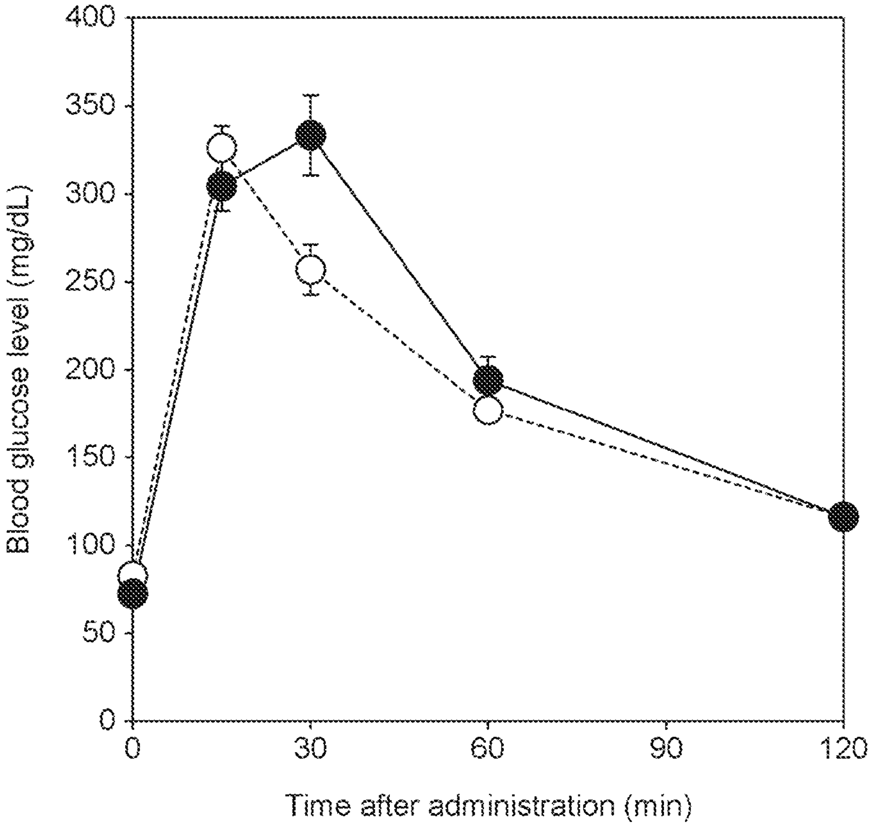

FIG. 5 shows the effects of Zizyphus extract on blood glucose levels. Blood glucose concentrations of male C57BL/6J mouse after an oral load with 2.5 g/kg body weight maltose with Zizyphus extract (each 500 mg/kg body weight) extracts (open circle). The control group was loaded with saline (closed circle). Each value represents the mean + SEM (n=5).

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term “a” or “an” used in relation to an entity is to be read to refer to one or more of that entity. As such, the terms “a” (or “an”), “one or more,” and “at least one” are used interchangeably herein.

As used herein, the term “comprise,” or variations thereof such as “comprises” or “comprising,” are to be read to Indicate the Inclusion of any recited Integer (e.g. a feature, element, characteristic, property, method/process step or limitation) or group of integers (e.g. features, element, characteristics, properties, method/process steps or limitations) but not the exclusion of any other integer or group of integers. Thus, as used herein the term “comprising” is inclusive or open-ended and does not exclude additional, unrecited integers or method/process steps.

The phrase “consisting essentially of” is used herein to require the specified integer(s) or steps as well as those which do not materially affect the character or function of the claimed invention.

As used herein, the term “consisting” is used to indicate the presence of the recited integer (e.g. a feature, element, characteristic, property, method/process step or limitation) or group of integers (e.g. features, element, characteristics, properties, method/process steps or limitations) alone.

As used herein, the term “disease” is used to define any abnormal condition that impairs physiological function and is associated with specific symptoms. The term Is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term “treatment” or “treating” refers to an intervention (e.g. the administration of an agent to a subject) which cures, ameliorates or lessens the symptoms of a disease or removes (or lessens the impact of) its cause(s) (for example, pathological variegated states). In this case, the term is used synonymously with the term “therapy”.

Additionally, the terms “treatment” or “treating” refers to an intervention (e.g. the administration of an agent to a subject) which prevents or delays the onset or progression of a disease or reduces (or eradicates) its incidence within a treated population. In this case, the term treatment is used synonymously with the term “prophylaxis”.

The term “subject” (which Is to be read to Include “individual”. “animal”, “patient” or “mammal” where context permits) defines any subject, particularly a mammalian subject, for whom treatment is indicated. Mammalian subjects include, but are not limited to, humans, domestic animals, farm animals, zoo animals, sport animals and pet animals. In preferred embodiments, the subject is a human.

As used herein, the term “energy utilization disease” encompasses any disease or disorder arising from abnormal energy utilization. The term therefore covers disorders and diseases of homeostasis, metabolic disease, dysfunction of sugar metabolism and appetite disorders. The term therefore includes insulin resistance, various forms of diabetes, metabolic syndrome, obesity, wasting syndromes (for example, cancer associated cachexia), myopathies, gastrointestinal disease, growth retardation, hypercholesterolemia, atherosclerosis and age-associated metabolic dysfunction. The term also covers conditions associated with metabolic syndrome, obesity and/or diabetes, including for example hyperglycaemia, glucose intolerance, hyperinsulinaemia, glucosuria, metabolic acidosis, cataracts, diabetic neuropathy, diabetic nephropathy, diabetic retinopathy, macular degeneration, glomerulosclerosis, diabetic cardiomyopathy, insulin resistance, impaired glucose metabolism, arthritis, hypertension, hyperlipidemia, osteoporosis, osteopenia, bone loss, brittle bone syndromes, acute coronary syndrome, infertility, short bowel syndrome, chronic fatigue, eating disorders and intestinal motility dysfunction.

The term “metabolic syndrome” is used herein to define conditions characterized by the presence of three or more of the following symptoms: central obesity (waist measurement of more than 40 inches for men and more than 35 inches for women); high levels of triglycerides (150 mg/dL or higher); low levels of HDL (below 40 mg/dL for men and below 50 mg/dL for women) and high blood pressure (130/85 mm Hg or higher).

The term therefore includes conditions defined in accordance with the definition of metabolic syndrome by the World Health Organization: (a) fasting plasma glucose above 6.1 mmol/L; (b) blood pressure above 140/90 mm Hg; and (c) one or more of the following: (i) plasma triglycerides above 1.7 mmol/L; (i) HDL below 0.9 and 1.0 mmol/L (for men and women, respectively); (iii) a body mass index above 30 kg/m$^2$.

References herein to the treatment of metabolic syndrome are to be interpreted to include the treatment of any or all of the disorders associated with metabolic syndrome, Including in particular obesity (e.g. central obesity), and elevated serum triglycerides and diabetes (including type 1 and type 2 diabetes and insulin resistance).

References herein to the treatment of type 1 or type 2 diabetes are to be interpreted to include the treatment of type 1 and type 2 diabetes per se as well as pre-diabetes (incipient diabetes) and insulin resistance.

The term “pre-diabetes” or “incipient diabetes” defines conditions in which elevated levels of glucose or glycosylated haemoglobin are present in the absence of diabetes.

As used herein, an effective amount of a compound or composition defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject’s condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical Improvement. A therapeutic result need not be a complete cure.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may be unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may be unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The term pharmaceutically acceptable derivative as applied to the compounds of the invention define compounds which are obtained (or obtainable) by chemical derivatization of the parent compound of the invention. The pharmaceutically acceptable derivatives are therefore suitable for administration to or use in contact with the tissues of humans without undue toxicity, irritation or allergic response (i.e. commensurate with a reasonable benefit/risk ratio). Preferred derivatives are those obtained (or obtainable) by alkylation, esterification or acylation of the parent compounds. Thus, the pharmaceutically acceptable derivates of the compound of the invention includes N-oxides and esters thereof.

The pharmaceutically acceptable derivatives of the invention may retain some or all of the biological activities described herein. In some cases, the biological activity is increased by derivatization. The derivatives may act as pro-drugs, and one or more of the biological activities described herein may arise only after in vivo processing. Particularly preferred pro-drugs are ester derivatives which are esterified at one or more of the free hydroxyls and which are activated by hydrolysis in vivo. Derivatization may also augment other biological activities of the compound, for example bioavailability and/or glycosidase inhibitory profile. For example, derivatization may increase CNS penetration (e.g. penetration of the blood-brain barrier).

The term pharmaceutically acceptable salt defines any non-toxic organic or inorganic acid addition salt of the free base which are suitable for use in contact with the tissues of humans and lower animals without undue toxicity, irritation, allergic response and which are commensurate with a reasonable benefit/risk ratio. Suitable pharmaceutically acceptable salts are well known in the art. Examples are the salts with Inorganic acids (for example hydrochloric, hydrobromic, sulphuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid).

These salts and the free base compounds can exist in either a hydrated or a substantially anhydrous form. Crystalline forms, including all polymorphic forms, of the compounds of the invention are also contemplated and in general the acid addition salts of the compounds are crystalline materials which are soluble in water and various hydrophilic organic solvents and which in comparison to their free base forms, demonstrate higher melting points and an increased solubility.

In the present specification the term "alkyl" defines a straight or branched saturated hydrocarbon chain. The term "$C_1$-$C_6$ alkyl" refers to a straight or branched saturated hydrocarbon chain having one to six carbon atoms. Examples include methyl, ethyl, n-propyl, isopropyl, t-butyl, n-hexyl. The alkyl groups of the invention may be optionally substituted by one or more halogen atoms.

In the present specification the term "alkenyl" defines a straight or branched hydrocarbon chain having containing at least one carbon-carbon double bond. The term "$C_1$-$C_6$ alkenyl" refers to a straight or branched unsaturated hydrocarbon chain having one to six carbon atoms. Examples include ethenyl, 2-propenyl, and 3-hexenyl. The alkenyl groups of the invention may be optionally substituted by one or more halogen atoms.

In the present specification the term "alkynyl" defines a straight or branched hydrocarbon chain having containing at least one carbon-carbon triple bond. The term "$C_1$-$C_6$ alkynyl" refers to a straight or branched unsaturated hydrocarbon chain having one to six carbon atoms. Examples include ethynyl, 2-propynyl, and 3-hexynyl. The alkynyl groups of the invention may be optionally substituted by one or more halogen atoms.

The term phytochemical is used herein in a broad sense to encompass any chemical constituent of a plant, Including macromolecules and small molecules. Important examples include alkaloids (for example imino sugars and imino sugars acids, e.g. selected from the structural classes pyrrolidines, piperidines, pyrrolizidine, indolizidines, tropanes and nortropanes), carbohydrate analogues, phenolic compounds, terpenoids, enzyme inhibitors, glycosides, nucleotides, amino acids, lipids and sugars.

The term isolated as applied to the compounds of the invention is used herein to indicate that the compound exists in a physical milieu distinct from that in which it occurs in nature (or in the case of synthetic compound, is purified to some degree). For example, the isolated compound may be substantially isolated (for example purified) with respect to the complex cellular milieu in which it naturally occurs (or with respect to the some or all of the starting products, intermediates, buffers, solvents, reactants and/or co-products from which it is synthesised). The isolated compound may therefore take the form of an enriched fraction or extract of any of the botanical sources described herein.

When the isolated material (e.g. synthetic, non-naturally occurring compound) Is purified, the absolute level of purity is not critical and those skilled in the art can readily determine appropriate levels of purity according to the use to which the material is to be put. In the case of synthetic material, purity levels may be in the range 85-99% w/w, and may exceed 99% w/w. However, and particularly in cases where the material is isolated from natural sources, preferred are purity levels of at least 0.1% w/w, 0.2% w/w, 0.3% w/w, 0.4% w/w, 0.5% w/w, 0.6% w/w, 0.7% w/w, 0.8% w/w, 0.9% w/w, 1.0% w/w, 1.1% w/w, 1.2% w/w, 1.3% w/w, 1.4% w/w, 1.5% w/w, 1.6% w/w, 1.7% w/w, 1.8% w/w, 1.9% w/w or 2.0% w/w.

Particularly preferred are purity levels of at least 0.5-2.0% w/w, for example at least 0.8-1.5% w/w, for example at least about 1.0% w/w. Levels of 5-10% w/w may be readily obtained in cases where the material is isolated from natural sources, if necessary, by employing suitable enrichment techniques, such as ion exchange chromatography.

In some circumstances, the isolated compound forms part of a composition (for example a more or less crude extract containing many other substances) or buffer system, which may for example contain other components. In other circumstances, the isolated compound may be purified to essential homogeneity, for example as determined spectrophotometrically, by NMR or by chromatography (for example GC-MS of the trimethylsilyl-derivatives).

The term herbal medicine is used herein to define a pharmaceutical composition in which at least one active principle (e.g. the compound) is not chemically synthesized and is a phytochemical constituent of a plant. In most cases, this non-synthetic active principle is not isolated (as defined herein), but present together with other phytochemicals with which it is associated in the source plant. In some cases, however, the plant-derived bioactive principle(s) may be in a concentrated fraction or isolated (sometimes involving high degrees of purification). In many cases, however, the herbal medicine comprises a more or less crude extract, infusion or fraction of a plant or even an unprocessed whole plant (or part thereof), though in such cases the plant (or plant part) Is usually at least dried and/or milled. The herbal medicine may be in the form of a food supplement, a beverage or presented in unitary doses as a herbal pharmaceutical kit or pack.

The term herbal bod is used herein to define a composition in which at least one component is not chemically synthesized but rather is a phytochemical constituent of a plant. In most cases, this non-synthetic component is not purified, but present together with other phytochemicals with which it is associated in the source plant. In some cases, however, the plant-derived component(s) may be in a concentrated fraction or isolated (sometimes to high degrees of purity). In many cases, however, the herbal food additive comprises a more or less crude extract, infusion or fraction of a plant or even an unprocessed whole plant (or part thereof), though in such cases the plant (or plant part) is usually at least dried and/or milled. The term therefore includes herbal foods in the form of additives and supplements for use with foods and beverages.

The term bioactive principle is used herein to define a phytochemical which is necessary or sufficient for the pharmaceutical efficacy of the herbal medicament in which it is comprised. In the case of the present invention, the bioactive principle(s) comprise one or more of the 4-hydroxymethyl-N-methyl-prolines of the invention.

The term nutraceutical is used herein to define a food product (or isolate thereof) which provides physiological benefits or protects against disease. Preferred nutraceuticals of the invention have blood sugar regulatory activity and find application in the treatment of energy utilization diseases. Other nutraceuticals of the invention are anti-inflammatory.

The term standard specification is used herein to define a characteristic, or a phytochemical profile, which is correlated with an acceptable quality of the herbal medicine, cosmetic or nutraceutical. In this context, the term quality is used to define the overall fitness of the product for its intended use, and includes the presence of one or more of the 4-hydroxymethyl-N-methyl-prolines of the invention at an appropriate concentration.

The term phytochemical profile is used herein to define a set of characteristics relating to different phytochemical constituents.

In its broadest aspect, the present invention contemplates all optical isomers, racemic forms and diastereomers of the 4-hydroxymethyl-N-methyl-prolines of the invention. Thus, references to the 4-hydroxymethyl-N-methyl-prolines of the invention encompass the 4-hydroxymethyl-N-methyl-prolines as a mixture of diastereomers, as individual diastereomers, as a mixture of enantiomers as well as in the form of individual enantiomers.

Chemical Synthesis

The 4-hydroxymethyl-N-methyl-prolines described herein may be made by conventional methods. Methods of making heteroaromatic ring systems are well known in the art. In particular, methods of synthesis are discussed in Comprehensive Heterocyclic Chemistry, Vol. 1 (Eds.: A R Katritzky, C W Rees), Pergamon Press, Oxford, 1984 and Comprehensive Heterocyclic Chemistry II: A Review of the Literature 1982-1995 The Structure, Reactions, Synthesis, and Uses of Heterocyclic Compounds, Alan R. Katritzky (Editor). Charles W. Rees (Editor). E. F. V. Scriven (Editor), Pergamon Pr, June 1996. Other general resources which would aid synthesis of the compounds of interest include March's Advanced Organic Chemistry: Reactions, Mechanisms, and Structure, Wiley-Interscience: 5th edition (Jan. 15, 2001).

Extraction from/Detection in Botanical Sources

The 4-hydroxymethyl-N-methyl-prolines of the invention described herein may be isolated from natural sources.

For example, the compounds of the invention may be extracted and/or purified from a botanical source selected from: (a) plants of the genus *Zizyphus*; and (b) plants of the genus *Paullinia*. In preferred embodiments, the botanical source is selected from a plant species selected from: *Z. jujuba, Z. spina-christi, Z. lotus, Z. mauritiana, Z. joazeiro* and *P. cupana*.

Plant material from the above-referenced botanic sources may be used as starting material for the isolation and purification of the 4-hydroxymethyl-N-methyl-prolines for use according to the invention. The 4-hydroxymethyl-N-methyl-prolines of the invention are water-soluble and can be concentrated by anion exchange chromatography or cation exchange chromatography. Size exclusion methods can also be used to concentrate them. Thus, it will be appreciated that those skilled in the art can readily purify and Isolate the 4-hydroxymethyl-N-methyl-prolines of the invention using standard techniques.

Any suitable part of the botanical source may be used, and in preferred embodiments the source may comprise or consist essentially of plant parts selected from: fruit, seeds and leaves. Other parts, such as roots, stems and bark may also be used.

Suitable processes for extraction and/or purification Include processes comprising the steps of:

(a) providing material, for example plant parts selected from: fruit, fruit parts, fruit extracts, fruit juices, seeds, bark, roots and/or leaves from the botanical source;
(b) extracting a first sample of the material with a polar solvent to produce a polar extract and a non-polar residue;
(c) subjecting the polar extract of step (b) to ion-exchange chromatography to produce an extract enriched in ionic-compounds and a non-ionic residue;
(d) chromatographically fractionating the enriched extract of step (c) to yield one or more polar fractions enriched in ionic compounds and comprising one or more compounds of the invention.

Herbal Quality Control Aspects

Samples

The herbal samples used in the methods of the present invention may be dried plant material or aliquots of the herbal food additive in the form in which it is added to foodstuffs and beverages. Alternatively, the samples may be pre-processed in any of a wide variety of ways prior to characterization. Pre-processing may involve physical or chemical pre-processing, for example powdering, grinding, freezing, evaporation, filtration, pressing, spray drying, extrusion, supercritical solvent extraction and tincture production.

Preferably, the food additive sample is fractionated prior to characterization. Any suitable method of fractionation may be employed, including solvent extraction(s). In a preferred embodiment the sample is fractionated by ion-exchange chromatography to produce an extract enriched in polar compounds and a non-polar residue. In such embodiments, characterisation preferably comprises gas-liquid chromatography (GC), for example GC-MS. When GC is used, the enriched extract Is derivatized prior to chromatography.

In cases where the herbal food additive is administered or sold in the form of a whole plant (or part thereof), the plant material may be dried prior to use. Any convenient form of drying may be used, including freeze-drying, spray drying or air-drying.

Detection of 4-hydroxymethyl-N-methyl-prolines

Any suitable form of characterization of the food additive sample may be employed, including without limitation functional and/or physical and/or chemical characterization, sufficient to detect the presence or absence or measure the amount of 4-hydroxymethyl-N-methyl-prolines in the sample.

Where the samples are physically characterized, the characterization may be selected from: (a) quantification of the phytochemical component(s); and/or (b) measurement of the purity of the constituents; and/or (c) determination of molecular weight (or molecular weight distribution or various statistical functions thereof in the case of fractions which comprise a plurality of different phytochemical constituents); and/or (d) determination of the molecular formula (e) (e.g. by nuclear magnetic resonance); and/or (e) spectral analysis.

Spectral analysis is particularly preferred, and may produce any or all of the following spectra:

(a) mass spectra (e.g. the mass to charge (m/z) value versus abundance), and/or
(b) chromatographic data (e.g. spectra, column retention times, elution profiles etc), and/or
(c) photodiode array (PDA) spectra (e.g. In both UV and visible ranges), and/or
(d) electrochemical detection or evaporative fight scattering detection
(e) nuclear magnetic resonance (NMR) spectra (e.g. spectral data sets obtained via $^{1}H$ and/or $^{13}C$ NMR).

When used according to the invention, the spectral analysis may be coupled with fractionation and/or derivitization of the sample, for example by use of GC-MS and/or HPLC-PDA-MS.

Particularly preferred is the use of GC-MS to detect the presence or absence or measure the amount of 4-hydroxymethyl-N-methyl-prolines in the sample.

Where the samples are chemically characterized, the characterization may be selected from measurements of the chemical reactivity of phytochemical constituent(s), the solubility of phytochemical constituent(s), the stability and melting point of phytochemical constituent(s) or any combination thereof.

Where the samples are functionally characterized, the characterization may comprise a biological assay, for example selected from in vivo or in vitro assays, enzyme inhibition assays (for example sialidase inhibition), receptor binding assays, cellular assays (e.g. cell replication, cell-pathogen, cell-cell interaction and cell secretion assays), immunoassays, anti-microbial activity (e.g. bacterial and viral cell-binding and/or replication) assays, toxicity assays (e.g. $LD_{50}$ assays) or any combination thereof.

Solvent Extractions

Suitable polar solvents for use in the process of the invention include without limitation organic solvents such as organic alcohols. Preferred are ethanol and methanol, as well as ethanol/water or methanol/water mixtures. Preferably, the polar solvent is selected from 51 to 80% ethanol/water, 31 to 50% ethanol/water, and up to 30% ethanol/water. Particularly preferred is a polar solvent which is approximately 50% ethanol/water. Suitable non-polar solvents for use in removing unwanted components in the the processes of the invention include without limitation organic solvents such as hexane and dichloromethane (DCM) or chloroform. Particularly preferred is dichloromethane. The conditions (time, temperature, degree of agitation etc.) under which the extraction(s) are performed can be readily determined empirically and vary according to the nature of the sample, the nature of any pre-processing and the solvent system selected.

Chromatographic Fractionation

Chromatographic fractionation may comprise gas-liquid chromatography. Gas-liquid chromatography is a process whereby a complex mixture of volatile substances is separated into its constituents by partitioning the sample between an inert gas under pressure and a thin layer of non-volatile liquid coated on an inert support inside a heated column. In order to achieve a good separation of specific compounds in a mixture, it is crucial to use a column with the correct characteristics. The nature of the solid support, type and amount of liquid phase, method of packing, overall length and column temperature are important factors.

Those skilled in the art, by routine trial and error and by using common general knowledge, will be able readily to determine the appropriate column characteristics according to the circumstances, including inter alia the extract under study and the nature of the solvent used in the extraction and the types of chemicals expected in those solvents. Particularly preferred, and useful in many circumstances, are capillary columns coated with a non-polar liquid phase (25 m×0.22 mm id×0.25 μm BPX5 stationary phase, produced by SGE Ltd., or equivalents thereof).

Many compounds are unsuitable for direct injection into a gas chromatograph because of their high polarity, low volatility or thermal instability. Compounds that are highly hydroxylated are difficult to vapourise because of inter-molecular hydrogen bonding.

However, by replacing the hydroxyl hydrogens with other chemical groups, they can be made sufficiently volatile for GC analysis. The two most popular means of derivatising hydroxyl groups are acetylation and silylation, where acetylates [$CH_3CO$—O—R] or silyl ethers, e.g. trimethylsilyl (TMS) ethers [$(CH_3)_3Si$—O—R] are formed. Thus, in embodiments where the enriched extract is chromatographically fractionated on an analytical scale the phytochemical constituents of the enriched extract are preferably derivatized, for example by acylation or silylation. Particularly preferred is trimethyl silyl (TMS) derivatization.

Chromatographic fractionation may also comprise ion exchange chromatography. Ion-exchange chromatography partially purifies ionic species to concentrate them and remove contaminating substances. Those skilled in the art, by routine trial and error and using common general knowledge, will be able readily to identify suitable column packing materials and mobile phase(s), which will depend inter alia on the quantities to be fractionated, the extracts under study and the nature of the solvent used in the extraction. Particularly preferred in the methods of the present invention are strongly acidic cation exchange resins which can be used in either the free acid or hydrogen ($H^+$) form or in the ammonium ($NH_4^+$) salt form). These forms adsorb cations from solution and release an equivalent number of counter-ions back into solution (either $H^+$ or $NH_4^+$ ions, depending on the form used). Also preferred are strongly basic anion exchange resins when used in the hydroxide form (OH—).

Fraction Characterization

The form the characterization takes depends on the nature of the herbal medicine under study and the characterization techniques employed. In general, any or all of the following approaches may be used:

(a) Functional Characterization

The functional characterization may comprise a biological assay Biological assays may be carried out in vivo or in vitro, and may include enzyme inhibition assays (for example sialidase inhibition). Other biological assays include receptor binding assays, cellular assays (including cell replication, cell-pathogen and cell-cell Interaction and cell secretion assays), immunoassays, anti-microbial activity (e.g. bacterial and viral cell-binding and/or replication) assays and toxicity assays (e.g. $LD_{50}$ assays).

Functional characterization may also be carried out indirectly by a form of characterization which permits the identification of one or more indices of biological activity.

(b) Physical Characterization

This can take the form of quantification of the phytochemical component(s) present in any given fraction or at any other stage in the process, measurement of the purity of the constituents, determination of molecular weight (or molecular weight distribution or various statistical functions thereof in the case of fractions which comprise a plurality of different phytochemical constituents), determination of the molecular formula (e) (e.g. by nuclear magnetic resonance) and various spectral analyses.

Particularly useful spectral characteristics include:

- Mass spectra (e.g. the mass to charge (m/z) value versus abundance), and/or
- Chromatographic data (e.g. spectra, column retention times, elution profiles etc), and/or
- Photodiode array (PDA) spectra (e.g. in both UV and visible ranges), and/or
- electrochemical detection (ED) or evaporative light scattering (ELSD) detection; and/or
- Nuclear magnetic resonance (NMR) spectra (including spectral data sets obtained via $^1H$ and/or $^{13}C$ NMR).

Spectral characterization can be coupled with the fractionation step. For example, GC-MS and HPLC-PDA-MS-ED-ELSD can be used (as described herein) to couple the fractionation with the obtention of mass spectral, UV-visible spectral, electrochemical response or fraction mass data and chromatographic spectral data.

Any or all of the above characteristics can be used to define a "chemical fingerprint" for any given sample (or any fraction or phytochemical constituent thereof).

(c) Chemical Characterization

This can take the form of measurements inter alia of the chemical reactivity of phytochemical constituent(s), their solubility, stability and melting point.

Medical Uses of the Compounds of the Invention

Neoplasia

The compounds of the invention are sialidase inhibitors, and so find application in the treatment or prophylaxis of diseases and disorders mediated by sialidase activity and/or sialic acid.

Sialidases are involved in a variety of pathological processes, including bacterial and viral infections and neoplasia, which makes these enzymes an attractive therapeutic target. The expression of the sialidases Neu1 and Neu3 appear to be altered in diabetes (e.g. Neu1 activity discussed by Natori, Y., et al, 2013, Biol. Pharm., Bull., 36, 1027). Sialidases are also implicated in atherogenesis (Sukhorukov, V. N., et al., 2017. Curr. Pharm. Des., 23, 4696) and osteo-arthritis (Katoh, S., et al., 1999, J Immunol., 162, 5058).

The compounds of the invention therefore find application in the treatment or prophylaxis of neoplasia/proliferative disorders, as described in more detail below.

As used herein, the term "neoplasia" is used sensu stricto to define diseases involving the abnormal proliferation of neoplastic cells. The term includes benign, pre-cancerous and malignant neoplasia (as defined above) and is used synonymously with the term "proliferative disorder".

Neoplasia arises from inappropriately high levels of cell division and/or low levels of apoptosis or senescence in neoplastic cells which have acquired genetic or epigenetic changes which free them from normal physiological control (i.e. the cells have been "transformed"). Neoplasia typically produces structures known as neoplasms: abnormal masses of tissue, the growth of which exceeds and is uncoordinated with that of the normal tissues and which persists in the same excessive manner after cessation of the stimulus which evoked the change. While most neoplasms form large masses of tissue (solid tumours), some neoplasms form no such discrete tissue mass. These include cervical intraepithelial neoplasias, anal intraepithelial neoplasias and leukemia.

Neoplasia may be benign, potentially malignant or malignant. Benign neoplasias include uterine fibroids and melanocytic naevi (skin moles) which are not invasive and which do not transform or progress into malignant neoplasms. Potentially malignant (pre-cancerous) neoplasms include carcinoma in situ, which is not invasive but which in time transforms into a malignant neoplasm.

Malignant neoplasia gives rise to neoplasms (tumours) which invade and destroy the surrounding tissue, may form metastases and eventually kill the host. The terms "malignant neoplasia" and "cancer" are used as synonyms herein.

The terms "proliferative disorder" and "neoplasia" may be used herein as synonyms to define a class of diseases which involve the pathological growth of cells in vivo.

Proliferative disorders therefore include cancer, cancer metastasis, smooth muscle cell proliferation, systemic sclerosis, cirrhosis of the liver, adult respiratory distress syndrome, idiopathic cardiomyopathy, lupus erythematosus, retinopathy (e.g. diabetic retinopathy), cardiac hyperplasia, benign prostatic hyperplasia, ovarian cysts, pulmonary fibrosis, endometriosis, fibromatosis, harmatomas, lymphangiomatosis, sarcoidosis and desmoid tumours. Neoplasia involving smooth muscle cell proliferation include hyperproliferation of cells in the vasculature (e.g. intimal smooth muscle cell hyperplasia, restenosis and vascular occlusion, including in particular stenosis following biologically- or mechanically-mediated vascular injury, such as angioplasty). Moreover, intimal smooth muscle cell hyperplasia can Include hyperplasia in smooth muscle other than the vasculature (e.g. blockage of the bile duct, bronchial airways and in the kidneys of patients with renal interstitial fibrosis). Non-cancerous proliferative disorders also include hyperproliferation of cells in the skin such as psoriasis and its varied clinical forms, Reiter's syndrome, *Pityriasis rubra* pilaris and hyperproliferative variants of disorders of keratinization (including actinic keratosis, senile keratosis and scleroderma).

The term "neoplasia" is also used herein sensu late to define diseases involving the abnormal growth and/or differentiation of cells in vivo, so encompassing hyperplasia, metaplasia and dysplasia.

Hyperplasia defines conditions in which normal (untransformed) cells within an organ or tissue proliferate to an abnormal extent. It may therefore result in the gross enlargement of an organ, the formation of a benign tumour, or may be visible only under a microscope. Hyperplasia is a physiological response to a specific stimulus and the hyperplastic cells remain subject to normal regulatory control mechanisms (unlike neoplastic growth, in which cells proliferate in an abnormal manner which is unresponsive to normal physiological control). Examples include congenital adrenal hyperplasia, endometrial hyperplasia, benign prostatic hyperplasia (prostate enlargement), hyperplasia of the breast (including ductal hyperplasia), focal epithelial hyperplasia (Heck's disease), sebaceous hyperplasia and liver hyperplasia.

Metaplasia defines conditions in which cells of one mature, differentiated type are replaced by cells of another mature, differentiated type. Examples include squamous metaplasia of the columnar epithelial cells of salivary gland ducts (when stones are present), squamous metaplasia of the transitional epithelium of the bladder (again, when stones are present or associated with infection), glandular metaplasia of the oesophagus in patients with gastric acid reflux (Barrett's esophagus) and osseous metaplasia in connective tissue.

Dysplasia defines conditions characterized by the abnormal maturation of cells within a tissue. This generally consists of an expansion of immature cells, with a corresponding decrease in the number and location of mature cells. For example, epithelial dysplasia of the cervix is characterized by an increased population of immature cells which are restricted to the mucosal surface. Myelodysplastic syndromes, or dysplasia of blood-forming cells, show increased numbers of immature cells in the bone marrow and a decrease in mature, functional cells in the blood. Other examples Include neurofibromatosis.

Hyperplasia, metaplasia, and dysplasia are generally reversible conditions, being the result of a stimulus (e.g. insult or injury). In contrast, neoplasia is generally irreversible and associated with cellular transformation.

The compounds of the invention find general application in the treatment of any neoplasia, including proliferative disorders, benign, pre-cancerous and malignant neoplasia, hyperplasia, metaplasia and dysplasia.

The invention therefore finds application in the treatment of proliferative disorders which include, but are not limited to cancer, cancer metastasis, smooth muscle cell proliferation, systemic sclerosis, cirrhosis of the liver, adult respiratory distress syndrome, idiopathic cardiomyopathy, lupus erythematosus, retinopathy (e.g. diabetic retinopathy), cardiac hyperplasia, benign prostatic hyperplasia, ovarian cysts, pulmonary fibrosis, endometriosis, fibromatosis, harmatomas, lymphangiomatosis, sarcoidosis and desmoid tumours. Neoplasia involving smooth muscle cell proliferation include hyperproliferation of cells in the vasculature (e.g. intimal smooth muscle cell hyperplasia, restenosis and vascular occlusion, including in particular stenosis following biologically- or mechanically-mediated vascular Injury, such as angioplasty). Moreover, Intimal smooth muscle cell hyperplasia can include hyperplasia in smooth muscle other than the vasculature (e.g. blockage of the bile duct, bronchial airways and in the kidneys of patients with renal interstitial fibrosis). Non-cancerous proliferative disorders also include hyperproliferation of cells in the skin such as psoriasis and its varied clinical forms, Reiter's syndrome, *Pityriasis rubra* pilaris and hyperproliferative variants of disorders of keratinization (including actinic keratosis, senile keratosis and scleroderma).

Particularly preferred is the treatment of malignant neoplasia (cancer). The invention finds application in the treatment of any cancer, including those selected from the following major groupings: (a) carcinoma; (b) blastoma; (c) leukemia; (d) lymphoma; (e) myeloma; (f) sarcoma and (g) cancers of mixed type.

Carcinoma refers to a malignant neoplasm of epithelial origin or cancer of the internal or external lining of the body. Carcinomas, malignancies of epithelial tissue, account for 80 to 90 percent of all cancer cases. Epithelial tissue is found throughout the body. It is present in the skin, as well as the covering and lining of organs and internal passageways, such as the gastrointestinal tract. In preferred embodiments the carcinoma treated according to the invention is selected from carcinomas of: salivary glands; colon; rectum; appendix; lung; thymus; breast; cervix uteri; bladder and eye.

The invention finds application in the treatment of all blastomas, including hepatoblastomas (e.g. nephroblastomas, nonepithelial renal tumours, rhabdoid renal tumour, kidney sarcomas and pPNET of the kidney), medulloblastomas, pancreatoblastomas, pulmonary blastoma, pleuropulmonary blastoma, neuroblastomas (including peripheral nervous cell tumours in general as well as ganglioneuroblastoma and retinoblastomas).

The invention finds application in the treatment of all leukemias, myeloproliferative diseases and myelodysplastic diseases, including: lymphoid leukemias (for example precursor cell leukemias, mature B-cell leukemias, mature T-cell leukemias and NK cell leukemias); acute myeloid leukemias: chronic myeloproliferative diseases; myelodysplastic syndrome and other myeloproliferative diseases. The invention therefore finds application in the treatment of various leukemias, including lymphatic, lymphocytic, or lymphoblastic leukemia (malignancy of the lymphoid and lymphocytic blood cell series) and polycythemia vera or erythremia (malignancy of various blood cell products, but with red cells predominating).

Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Unlike the leukemias which are sometimes called “liquid cancers,” lymphomas are “solid cancers”. Lymphomas may also occur in specific organs such as the stomach, breast or brain. These lymphomas are referred to as extranodal lymphomas. The lymphomas are subclassified into two categories: Hodgkin lymphoma and Non-Hodgkin lymphoma. The presence of Reed-Stenberg cells in Hodgkin lymphoma diagnostically distinguishes Hodgkin lymphoma from Non-Hodgkin lymphoma. The invention finds application in the treatment of all such lymphomas and reticuloendothelial neoplasms, including: (a) Hodgkin lymphomas; (b) Non-Hodgkin lymphomas (for example precursor cell lymphomas, mature B-cell lymphomas, mature T-cell lymphomas and NK-cell lymphomas: (c) Burkitt lymphoma and (d) other lymphoreticular neoplasms, including mantle cell lymphoma.

The invention therefore finds application in the treatment of a wide range of lymphomas, including for example tumours of the glands or nodes of the lymphatic system (including the spleen, tonsils, and thymus) and extranodal lymphomas of the stomach, breast and brain.

Myeloma is cancer that originates in the plasma cells of bone marrow. The invention therefore finds application in the treatment of hematopoieitic tumours and haematological malignancies, including those of lymphoid lineage (e.g. leukaemia, acute lymphocytic leukaemia, chronic lymphocytic leukaemia, B-cell lymphoma (such as diffuse large B cell lymphoma), T-cell lymphoma, Hodgkin’s lymphoma, non-Hodgkin’s lymphoma (the presence of Reed-Stenberg cells in Hodgkin lymphoma distinguishes Hodgkin lymphoma from Non-Hodgkin lymphoma), hairy cell lymphoma and Burkitt’s lymphoma) as well as hematopoieitic tumours of myeloid lineage (for example acute myeloid leukaemia, chronic myeloid leukaemias, myelogenous leukaemias and Imatinib sensitive and refractory chronic myelogenous leukaemias, myelodysplastic syndrome, Bortezomib sensitive and refractory multiple myeloma, myeloproliferative disease or promyelocytic leukaemia and thyroid follicular cancer).

The Invention finds application in the treatment of all sarcomas. Sarcoma refers to cancer that originates in supportive and connective tissues such as bones, tendons, cartilage, muscle and fat. Generally occurring in young adults, the most common sarcoma often develops as a painful mass on the bone. Sarcoma tumours usually resemble the tissue in which they grow. Exemplary sarcomas for treatment according to the invention include osteosarcoma (or osteogenic sarcoma); chondrosarcoma; leiomyosarcoma (smooth muscle); rhabdomyosarcoma (skeletal muscle); mesothelial sarcoma or mesothelioma (membranous lining of body cavities); fibrosarcoma (fibrous tissue); angiosarcoma or hemangioendothelioma (blood vessels); liposarcoma; glioma; astrocytoma; myxosarcoma (primitive embryonic connective tissue) and mesenchymous or mixed mesodermal tumour (mixed connective tissue types). Fibrosarcomas include peripheral nerve sheath tumours and other fibrous neoplasms, for example fibroblastic and myofibroblastic tumours, nerve sheath tumours and other fibromatous neoplasms. Also included is Kaposi sarcoma. Also included are soft tissue sarcomas, for example Ewing tumour and Askin tumour of soft tissue, pPNET of soft tissue, extrarenal rhabdoid tumour; fibrohistiocytic tumours; synovial sarcomas; osseous and chondromatous neoplasms of soft tissue and alveolar soft parts sarcoma. Osteosarcomas (malignant bone tumours) include: malignant fibrous neoplasms of bone; malignant chordomas and odontogenic malignant tumours. Gliomas Include oligodendrogliomas, mixed and unspecified gliomas and neuroepithelial glial tumours.

The invention finds application in the treatment of cancers of the mixed type, including for example adenosquamous carcinoma, mixed mesodermal tumour, carcinosarcoma and teratocarcinoma. The Invention therefore finds application in the treatment of various CNS, PNS and miscellaneous intracranial and intraspinal neoplasms, including: astrocytoma, neuroblastoma, glioma, schwannoma, ependymomas and choroid plexus tumour (for example ependymomas and choroid plexus tumours); intracranial and intraspinal embryonal tumours (for example medulloblastomas, primitive neuroectodermal tumour (PNET), medulloepithelioma, atypical teratoid/rhabdoid tumour and other intracranial and intraspinal neoplasms (for example pituitary adenomas and carcinomas, tumours of the sellar region (craniopharyngiomas), pineal parenchymal tumours, neuronal and mixed neuronal-glial tumours, meningiomas and intracranial and intraspinal neoplasms in general).

Thus, the invention finds particular application in the treatment of: intracranial and intraspinal germ cell tumours; intracranial and intraspinal germinomas; intracranial and intraspinal teratomas; Intracranial and intraspinal embryonal carcinomas; Intracranial and intraspinal yolk sac tumour; intracranial and intraspinal choriocarcinoma and intracranial and intraspinal tumours of mixed forms.

The invention also finds application in the treatment of various germ cell tumours, trophoblastic tumours and neoplasms of the gonads. Thus, the invention finds application in the treatment of malignant extracranial and extragonadal germ cell tumours include, for example, malignant germinomas of extracranial and extragonadal sites, malignant teratomas of extracranial and extragonadal sites, embryonal carcinomas of extracranial and extragonadal sites, yolk sac tumour of extracranial and extragonadal sites; choriocarcinomas of extracranial and extragonadal sites and malignant mixed germ cell tumours of extracranial and extragonadal sites in general. The invention also finds application in the treatment of malignant gonadal germ cell tumours, including for example malignant gonadal germinomas, seminomas, malignant gonadal teratomas, gonadal embryonal carcinomas, gonadal yolk sac tumour, gonadal choriocarcinoma, malignant gonadal tumours of mixed forms and malignant gonadal gonadoblastoma.

Infectious Disease

The compounds of the invention are sialidase inhibitors, and so find application in the treatment or prophylaxis of diseases and disorders mediated by sialidase activity and/or sialic acid. Such diseases and disorders include infectious diseases (including bacterial and viral infections).

The compounds of the present invention may have anti-infective (e.g. pathostatic or pathocidal) activity against any infective agent. The compounds of the invention may therefore target (i.e. have activity against) a wide range of different infectious agents. Thus, the invention finds broad application in the treatment or prevention of any infection or infectious disease, including infectious diseases in which viral, bacterial, fungal, protozoal, prion or metazoan agents are implicated.

Thus, the invention finds broad application in the treatment or prevention of viral infection; the treatment or prevention of bacterial infection; the treatment or prevention of protozoal infection; the treatment or prevention of fungal infection; the treatment or prevention of prion Infection; and/or the treatment or prevention of metazoan (e.g. helminth) Infection or infestation. The compounds of the invention may also find application in the treatment or prevention of chroni, dormant or latent viral, bacterial, protozoal, fungal, prion or metazoan (e.g. helminth) infections or infestations.

Viral targets include but are not limited to the following viruses (or virus classes): Retroviridae (e.g. the human immunodeficiency viruses, including HIV-1); Picornaviridae (e.g. polio viruses, hepatitis A virus; enteroviruses, human Coxsackie viruses, rhinoviruses, echoviruses); Caldviridae (e.g. strains that cause gastroenteritis); Togaviridae (e.g. equine encephalitis viruses, rubella viruses): Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses): Arena viridae (hemorrhagic fever viruses); Reoviridae (e.g. reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the HCV virus (causing non-A, non-B hepatitis); Norwalk and related viruses, and astroviruses). Of the foregoing, particularly preferred are HIV, Hepatitis A, Hepatitis B, Hepatitis C, rabies virus, poliovirus, influenza virus, meningitis virus, measles virus, mumps virus, rubella, pertussis, encephalitis virus, papilloma virus, yellow fever virus, respiratory syncytial virus, parvovirus, chikungunya virus, haemorrhagic fever viruses and Herpes viruses, particularly, varicella, cytomegalovirus and Epstein-Barr virus.

Bacterial targets include but are not limited to both Gram-negative and Gram-positive bacteria. Examples of bacteria which may be targeted by the compounds of the invention include but are not limited to: *Helicobacter pylori, Borelia burgdorferi, Legionella pneumophilia, Mycobacterium* spp (e.g. *M. tuberculosis, M. leprae, M. avium, M. intracellulare, M. kansaii* and *M. gordonae*), *Staphylococcus aureus, Neisseria gonorrhoeae, Neisseria meningitidis, Listeria monocytogenes. Streptococcus pyogenes* (Group A *Streptococcus*), *Streptococcus agalactiae* (Group B *Streptococcus*), *Streptococcus viridans, Streptococcus faecalis, Streptococcus bovis*, any anaerobic species of the genus *Streptococcus, Streptococcus pneumoniae, Campylobacter* spp., *Enterococcus* spp., *Haemophilus influenzae, Bacillus anthracis, Corynebacterium* spp. (including *C. diphtheriae*), *Erysipelothrix rhusiopathiae, Clostridium perfringens, Clostridium tetani, Enterobacter aerogenes, Klebsiella* spp (including *K. pneumoniae*). *Pasteurella multocida, Bacteroides* spp., *Fusobacterium nucleatum, Streptobacillus monilijormis, Treponema pallidium, Treponema pertenue, Leptospira* spp., *Rickettsia* spp. and *Actinomyces* spp. (including *A. israelii*). Bacteria which form biofilms in vivo are particular targets of the compounds of the Invention, and these include *Tannerella forsythia, Tannerella denticola, Porphyromonas gingivalis* and *Gardnerella vaginalis.*

Fungal targets include but are not limited to *Cryptococcus neoformans, Histoplasma capsulatum, Coccidioides immitis, Blastomyces dermatitidis, Chlamydia trachomatis* and *Candida albicans.*

Protozoal targets include but are not limited to *Plasmodium* spp. (including *Plasmodium falciparum, Plasmodium malariae, Plasmodium ovale* and *Plasmodium vivax*), *Toxoplasma* spp. (including *T. gondii* and *T. cruzii*), *Leishmania* spp., *Cryptosporidium* spp. (including *C. parvum*), *Cyclospora* spp. (including *C. cayetanensis*), *Entamoeba* (including *E. histolytica*) and Giardia spp. (including *G. lamblia*).

Metazoan targets include parasites or pathogens, such as helminths (e.g. *Schistosoma* spp.).

Inhibition of Bacterial Growth In Vivo

The sialidase inhibitory properties of the compounds of the invention also find application in the inhibition of commensal and/or pathogenic bacterial growth in vivo, and in particular in disrupting host-bacterial cell interactions, including the inhibition or elimination of bacterial biofilms in a mammalian (e.g. human) host.

The compounds therefore find application in the treatment or prophylaxis of diseases and disorders mediated or characterized by the presence of bacterial biofilms (for example, sub-gingival plaque biofilms and mucosal biofilms).

Such diseases include periodontal diseases, bacterial vaginosis and diseases caused by infection with *Tannerella forsythia, Tannerella denticola, Porphyromonas gingivalis* and *Gardnerella vaginalis* (the latter species being associated with bacterial vaginosis and pre-term birth).

Atherogenesis

The compounds of the invention are sialidase inhibitors, and so find application in the treatment or prophylaxis of atherogenesis, since sialidases are involved in this process (Sukhorukov, V. N., et al., 2017, Curr. Pharm. Des., 23, 4696) and osteo-arthritis (Katoh, S., et al., 1999, J Immunol., 162, 5058). Thus, the compounds of the Invention find application in the treatment and prophylaxis of atherosclerosis.

Modulation of Commensal Bacterial Growth

The sialidase inhibitory properties of the compounds of the invention also find application in the modulation of the composition of the microbiota (and in particular commensal bacteria) in a host, for example modulating the composition of commensal bacteria in mammalian (e.g. human) hosts. Particularly preferred is modulation of the gut microbiota.

Inflammation

The compounds of the invention inhibit sialidases which are thought to be involved in the TNF-α induced inflammatory process in osteo-arthritis Gee, K. et al., 2003, J Biol Chem. 278, 37275). Furthermore, the compounds of the invention can suppress or inhibit TNF-α activity. As such, they find application in any disorder in which inflammation plays a role in the impairment of physiological function and/or symptoms and/or pain. For example, the compounds of the Invention may be used as anti-Inflammatories, for example to reduce or eliminate acute, chronic, local or systemic inflammation.

Inflammation occurs when tissues are injured by microorganisms, trauma, chemicals, heat, cold, sunburn or any other harmful events. Endogenous chemicals (for example, bradykinin, histamine and serotonin) are released on injury or insult, and such chemicals activate and attract tissue macrophages and other white blood cells. During this process, chemical mediators such as TNF-α are released, giving rise to inflammation.

Inflammatory disorders are those in which the inflammation is sustained or chronic. In such circumstances, prolonged inflammation causes tissue destruction and results in extensive damage and eventual failure of the effected tissue and/or organ.

Thus, the compounds of the invention find application in the treatment of non-localized inflammatory disorders, for example those affecting more than one organ Such disorders Include those arising from Immune dysfunction (and may therefore have an autoimmune component). Such conditions include systemic lupus erythematosus (SLE), scleroderma and hypersensitivities.

The compounds of the invention also find application in the treatment of localized inflammatory disorders, including skin inflammation and chronic prostatitis, glomerulonephritis, inflammatory bowel diseases, pelvic inflammatory disease, reperfusion injury, rheumatoid arthritis, transplant rejection, vasculitis, asthma, acne, osteoarthritis, oral mucosal, gastrointestinal inflammation, ocular, nasal and aural inflammation and other steroid responsive inflammatory disorders.

In particular, the compounds of the invention find application in the treatment of cutaneous inflammatory diseases. These include, for example, actinic keratosis, acne (including acne vulgaris, comedonal, acne rosacea, and nodulocystic acne), allergic contact dermatitis, angioedema, bullous pemiphigoid, cutaneous drug reactions, erythema multiforme, lupus erythrametosus, photodermatitis, psoriatic arthritis, scleroderma and urticaria, psoriasis, dermatitis (e.g. atopic dermatitis), scleroderma, steroid-responsive cutaneous inflammatory disorders (for example uremic pruritus) and skin conditions associated with exposure to sun, radiation, chemotherapy and environmental irritants.

The compounds of the Invention also find application in the treatment of Inflammatory autoimmune diseases. Such diseases may involve specific tissues or organs (such as the musculoskeletal tissue, as in rheumatoid arthritis and ankylosing spondylitis), the GI tract (as for example in Crohn's disease and ulcerative colitis), the CNS (as for example in Alzheimer's disease, multiple sclerosis, motor neurone disease, Parkinson's disease and chronic fatigue syndrome), pancreatic beta cells (for example insulin-dependent diabetes mellitus), the adrenal gland (for example Addison's disease), the kidney (for example Goodpasture's syndrome, IgA nephropathy and interstitial nephritis), exocrine glands (for example Sjogren's syndrome and autoimmune pancreatitis) and the skin (for example psoriasis and atopic dermatitis).

Other inflammatory disorders treatable according to the present invention include conditions such as osteoarthritis, periodontal disease, diabetic nephropathy, chronic obstructive pulmonary disease, artherosclerosis, graft versus host disease, chronic pelvic inflammatory disease, endometriosis, chronic hepatitis and tuberculosis.

Energy Utilization Diseases

The compounds of the invention have blood sugar regulating activities. The invention therefore finds application in the treatment of various energy utilization diseases. These diseases encompass a wide range of diseases and disorders and include, for example, disorders of homeostasis, metabolic diseases, dysfunction of sugar metabolism and appetite disorders.

Examples of energy utilization diseases therefore include insulin resistance, various forms of diabetes (including type 1 and type 2 diabetes), metabolic syndrome, obesity, wasting syndromes (for example, cancer associated cachexia), myopathies, gastrointestinal disease, growth retardation, hypercholesterolemia, atherosclerosis and age-associated metabolic dysfunction.

Energy utilization diseases also include conditions associated with metabolic syndrome, obesity and/or diabetes, including for example hyperglycaemia, glucose intolerance, hyperinsulinaemia, glucosuria, metabolic acidosis, cataracts, diabetic neuropathy, diabetic nephropathy, diabetic retinopathy, macular degeneration, glomerulosclerosis, diabetic cardiomyopathy, Insulin resistance, impaired glucose metabolism, arthritis, hypertension, hyperlipidemia, osteoporosis, osteopenia, bone loss, brittle bone syndromes, acute coronary syndrome, infertility, short bowel syndrome, chronic fatigue, eating disorders and intestinal motility dysfunction.

Insulin Resistance, Metabolic Syndrome and Diabetes

In healthy individuals, blood glucose levels are maintained within a narrow range by two pancreatic hormones: insulin (produced by pancreatic β-cells) and glucagon (produced by pancreatic α-cells). Pancreatic β-cells sense increases in blood glucose levels and respond by secreting insulin. Insulin promotes glucose uptake by tissues of the body, thereby restoring blood glucose concentration to the physiological range. Glucagon acts reciprocally, increasing blood glucose levels under fasting conditions, primarily by stimulating glucose production in the liver.

Insulin resistance is characterized by a reduced action of insulin in skeletal muscle, adipocytes and hepatocytes so that normal amounts of insulin become inadequate to produce a normal insulin response from the cells of these tissues. In adipocytes, insulin resistance results in hydrolysis of stored triglycerides, leading to elevated free fatty acids in the blood plasma. In muscle, insulin resistance reduces glucose uptake while in hepatocytes it reduces glucose storage. In both of the latter cases an elevation of blood glucose concentrations results.

High plasma levels of insulin and glucose due to insulin resistance often progresses to metabolic syndrome and type 2 diabetes.

Metabolic syndrome is a constellation of abnormalities and disorders that increase the risk of cardiovascular disease and diabetes. The incidence is very high in many developed countries: some studies indicate prevalence in the USA of up to 25% of the population. The disorder is also known as (metabolic) syndrome X, insulin resistance syndrome. Reaven's syndrome and CHAOS. Metabolic syndrome may be diagnosed by the presence of three or more of the following symptoms: central obesity (waist measurement of more than 40 inches for men and more than 35 inches for women); high levels of triglycerides (150 mg/dL or higher); low levels of HDL (below 40 mg/dL for men and below 50 mg/dL for women) and high blood pressure (130/85 mm Hg or higher). Associated diseases and signs are: fatty liver (often progressing to non-alcoholic fatty liver disease), polycystic ovarian syndrome, hemochromatosis (iron overload) and acanthosis nigricans (dark skin patches).

The first line treatment of metabolic syndrome is change of lifestyle (caloric restriction and physical activity). However, drug treatment is frequently required. Generally, the individual diseases that comprise the metabolic syndrome are treated separately (e.g. diuretics and ACE inhibitors for hypertension). Cholesterol drugs may be used to lower LDL cholesterol and triglyceride levels, if they are elevated, and to raise HDL levels if they are low. Use of drugs that decrease insulin resistance (e.g. metformin and thiazolidinediones is controversial). Cardiovascular exercise is therapeutic in less than 31% of cases and does not generally produce a decrease in fasting plasma glucose or insulin resistance.

Thus, new and/or alternative treatments for metabolic syndrome are required, particularly treatments which are effective against obesity and/or elevated triglyceride levels.

Type 2 diabetes is a chronic disease that is characterised by persistently elevated blood glucose levels (hyperglycaemia). Insulin resistance together with Impaired insulin secretion from the pancreatic β-cells characterizes the disease. The progression of insulin resistance to type 2 diabetes is marked by the development of hyperglycaemia after eating when pancreatic β-cells become unable to produce adequate insulin to maintain normal blood sugar levels (euglycemia).

The most important drug currently used to treat type 2 diabetes is metformin (Glucophage. Diabex, Diaformin, Fortamet, Riomet, Glumetza, Cidophage and others). Metformin is of the biguanide class of oral antihyperglycaemic agents. Other biguanides include phenformin and buformin (now withdrawn). Metformin works primarily by reducing liver release of blood glucose from glycogen stores, but also has some effect in increasing the uptake of glucose. Other widely used drug classes include those of the sulfonylurea group (including glibenclamide and gliclazide). These drugs increase glucose stimulated insulin secretion by the pancreas. Newer drug classes include thiazolidinediones (e.g. rosiglitazone, pioglitazone, and troglitazone), which act by binding to PPARs (peroxisome proliferator-activated receptors), a group of receptor molecules inside the cell nucleus. Other classes include α-glucosidase inhibitors (acarbose), meglitinides (which stimulate insulin release and include nateglinide, repaglinide and their analogues), peptide analogues (e.g. Incretin mimetics, which act as Insulin secretagogues, glucagon-like peptide analogues (e.g. exenatide), dipeptidyl peptidase-4 (DPP-4) inhibitors (which increase incretin levels (e.g. sitagliptin) and amylin agonist analogues (which slow gastric emptying and suppress glucagon (e.g. pramlintide).

However, no existing therapies for the different forms of type 2 diabetes seem to improve function of key intrinsic factors in the β-cells and all existing therapies fail to arrest progression of the disease and, over time, also fail to normalise glucose levels and/or prevent subsequent complications. The existing therapies are also associated with undesirable side effects. For example, insulin secretagogues and insulin injections may cause hypoglycaemia and weight gain. Patients may also become unresponsive to insulin secretagogues over time. Metformin and α-glucosidase inhibitors often lead to gastrointestinal problems and PPAR agonists tend to cause increased weight gain and oedema. Exenatide is also reported to cause nausea and vomiting.

Glycosylation has an Important role in regulating properties of proteins and Is associated with many diseases. Itoh, N et al., 2007 (*Am J Physiol Endocrinol Metab* 293: E1069-E1077) have reported the serum N-glycan profile in human subjects with type 2 diabetes and found an increased amount of a biantennary N-glycan that had an α1,6-fucose with a bisecting N-acetylglucosamine. Copeland, R. J. et al., 2008 (*Am J Physiol Endocrinol Metab* 295: E17-E28) have reviewed the importance of O-linked N-acetylglucosamine in diabetes and concluded that there is a strong positive correlation between GlcNAcylation and the development of insulin resistance. O-linked-β-N-acetylglucosamine (O-GlcNAc) Is a dynamic posttranslational modification that, analogous to phosphorylation, cycles on and off serine and/or threonine hydroxyl groups. Cycling of O-GlcNAc is regulated by the concerted actions of O-GlcNAc transferase and O-GlcNAcase. GlcNAcylation is involved in the aetiology of glucose toxicity and chronic hyperglycemia-induced insulin resistance, a major hallmark of type 2 diabetes. Hexosaminidase activity has been shown to be elevated in the serum of diabetics (e.g. Agardh, C. D. et al., 1982, Acta Med Scand. 212:39-41).

Type 1 diabetes (or insulin dependent diabetes) is characterized by loss of the insulin-producing beta cells of the islets of Langerhans in the pancreas, leading to a deficiency of insulin. The main cause of this beta cell loss is a T-cell mediated autoimmune attack. There is no known preventative measure that can be taken against type 1 diabetes, which comprises up to 10% of diabetes mellitus cases in North America and Europe. Most affected people are otherwise healthy and of a healthy weight when onset occurs. Sensitivity and responsiveness to insulin are usually normal, especially in the early stages.

The principal treatment of type 1 diabetes, even from the earliest stages, is replacement of insulin combined with careful monitoring of blood glucose levels using blood-testing monitors. Without insulin, ketosis and diabetic ketoacidosis can develop and coma or death will result. Apart from the common subcutaneous injections, it is also possible to deliver insulin by a pump, which allows continuous infusion of insulin 24 hours a day at preset levels, and the ability to program doses (a bolus) of insulin as needed at meal times. An inhaled form of insulin, Exubera, has recently been approved by the FDA.

The treatment of type 1 diabetes must be continued indefinitely. While treatment does not impair normal activities, great awareness, appropriate care, and discipline in testing and medication must be observed.

Thus, new and/or alternative antidiabetic drug treatments, particularly those that are able to restore β-cell function, are required. In particular, there is a real and substantial unmet clinical need for an effective drug that is capable of treating both type 2 and type 1 diabetes and associated conditions with fewer side effects than existing drug therapies.

The invention finds broad application in the treatment of any energy utilization disease. Thus, diseases which may be treated according to the invention include, for example, disorders of homeostasis, metabolic diseases, dysfunction of sugar metabolism and appetite disorders.

In preferred embodiments, the invention finds application in the treatment of insulin resistance, various forms of diabetes, metabolic syndrome, obesity, wasting syndromes (for example, cancer associated cachexia), myopathies, gastrointestinal disease, growth retardation, hypercholesterolemia, atherosclerosis and age-associated metabolic dysfunction.

The invention may also be used for the treatment of conditions associated with metabolic syndrome, obesity and/or diabetes, including for example hyperglycaemia, glucose intolerance, hyperinsulinaemia, glucosuria, metabolic acidosis, cataracts, diabetic neuropathy, diabetic nephropathy, diabetic retinopathy, macular degeneration, glomerulosclerosis, diabetic cardiomyopathy, Insulin resistance, Impaired glucose metabolism, arthritis, hypertension, hyperlipidemia, osteoporosis, osteopenia, bone loss, brittle bone syndromes, acute coronary syndrome, infertility, short bowel syndrome, chronic fatigue, eating disorders, intestinal motility dysfunction and sugar metabolism dysfunction.

The invention may also be used to suppress appetite. Without wishing to be bound by any theory, this may be effected by the maintenance of even blood glucose levels, eliminating the large dips that cause tiredness/fatigue and desire to eat sweet things (i.e. by promoting an 'improved energy balance').

Particularly preferred is the treatment of insulin resistance, metabolic syndrome, obesity and diabetes (particularly type 2 diabetes).

The invention finds application in the treatment of insulin resistance. Insulin resistance is characterized by a reduced action of insulin in skeletal muscle, adipocytes and hepatocytes so that normal amounts of insulin become inadequate to produce a normal insulin response from the cells of these tissues. In adipocytes, insulin resistance results in hydrolysis of stored triglycerides, leading to elevated free fatty acids in the blood plasma. In muscle, insulin resistance reduces glucose uptake while in hepatocytes it reduces glucose storage. In both of the latter cases an elevation of blood glucose concentrations results. High plasma levels of insulin and glucose due to insulin resistance often progresses to metabolic syndrome and type 2 diabetes.

The invention finds application in the treatment of metabolic syndrome (as herein defined). The disorder is also known as (metabolic) syndrome X, insulin resistance syndrome, Reaven's syndrome and CHAOS.

The invention finds application in the treatment of diseases associated with metabolic syndrome, including for example: fatty liver (often progressing to non-alcoholic fatty liver disease), polycystic ovarian syndrome, hemochromatosis (iron overload) and acanthosis nigricans (dark skin patches).

The invention finds application in the treatment of diabetes, including type 1 and type 2 diabetes. Type 2 diabetes Is a chronic disease that Is characterised by persistently elevated blood glucose levels (hyperglycaemia). Insulin resistance together with impaired insulin secretion from the pancreatic β-cells characterizes the disease. The progression of insulin resistance to type 2 diabetes is marked by the development of hyperglycaemia after eating when pancreatic β-cells become unable to produce adequate insulin to maintain normal blood sugar levels (euglycemia)).

Type 1 Diabetes

The invention finds application in the treatment of Type 1 diabetes (or insulin dependent diabetes). Type 1 diabetes is characterized by loss of the insulin-producing beta cells of the islets of Langerhans in the pancreas, leading to a deficiency of insulin. The main cause of this beta cell loss is a T-cell mediated autoimmune attack. There is no known preventative measure that can be taken against type 1 diabetes, which comprises up to 10% of diabetes mellitus cases in North America and Europe. Most affected people are otherwise healthy and of a healthy weight when onset occurs. Sensitivity and responsiveness to insulin are usually normal, especially in the early stages.

As explained below, the compounds of the invention may have antidiabetogenic virus activity. Diabetogenic viruses are aetiological agents of type 1 diabetes, and so compounds having antidiabetogenic virus activity are particularly preferred for use in the treatment or prevention of type 1 diabetes and also: (a) in the treatment of virus-induced type 1 diabetes; (b) in the delay or prevention of viral diabetogenesis; (c) the treatment of type 1 diabetes; (d) the treatment or prevention of virus-induced β-cell lysis (e.g. by non-immune cytolysis or by immune-mediated cytolysis); (e) the prevention, reduction or elimination of virus-mediated endogenous interferon production; (f) the prevention, reduction or elimination of virus-mediated bystander activation of autoreactive T cells targeted to β-cells; (g) the prevention, reduction or elimination of viral activation and/or expansion of autoreactive T cells targeted to β-cells; and/or (h) the prevention or reduction of virus-mediated loss of regulatory T cells exposing β-cells to immune-mediated cytolysis.

Such applications find particular utility in the treatment of subjects having islet autoantibodies, since such patients are at high risk of progression to type 1 diabetes and may be infected with a diabetogenic virus as described above.

The invention also finds application in the treatment and management of mitochondrial diseases, and in particular acquired mitochondrial dysfunction associated with the foregoing energy utilization diseases.

Posology

The compounds of the present invention can be administered topically or by oral or parenteral routes, including intravenous, intramuscular, intraperitoneal, subcutaneous, transdermal, airway (aerosol), rectal, vaginal and topical (including buccal and sublingual) administration.

The amount administered can vary widely according to the particular dosage unit employed, the period of treatment, the age and sex of the patient treated, the nature and extent of the disorder treated, and the particular compound selected.

In general, the effective amount of the compound administered will generally range from about 0.01 mg/kg to 500 mg/kg daily. A unit dosage may contain from 0.05 to 500 mg of the compound, and can be taken one or more times per day. The compound can be administered with a pharmaceutical carrier using conventional dosage unit forms either orally, parenterally, or topically, as described below.

The preferred route of administration is oral administration. In general a suitable dose will be in the range of 0.01 to 500 mg per kilogram body weight of the recipient per day, preferably in the range of 0.1 to 50 mg per kilogram body weight per day and most preferably in the range 1 to 5 mg per kilogram body weight per day.

The desired dose is preferably presented as a single dose for daily administration. However, two, three, four, five or six or more sub-doses administered at appropriate intervals throughout the day may also be employed. These sub-doses may be administered in unit dosage forms, for example, containing 0.001 to 100 mg, preferably 0.01 to 10 mg, and most preferably 0.5 to 1.0 mg of active ingredient per unit dosage form.

Formulation

The compound for use according to the invention may take any form. It may be synthetic or isolated from natural sources (for example from any of the botanical sources identified herein, including for example a botanical source selected from plants of the family Rhamnaceae and Sapindaceae (for example, plants of the genus *Zizyphus* or *Paullinia*, e.g. plants of the species *Zizyphus jujuba*) or *Paullinia cupana*. Particularly preferred as botanical source are fruits, parts of fruits, fruit extracts and fruit juices of the foregoing plants.

When isolated from a natural source, the compound may be purified. However, the compositions of the invention may take the form of herbal medicines, as hereinbefore defined. Such herbal medicines preferably are analysed to determine whether they meet a standard specification prior to use.

The herbal medicines for use according to the invention may be dried plant material. Alternatively, the herbal medicine may be processed plant material, the processing involving physical or chemical pre-processing, for example powdering, grinding, freezing, evaporation, filtration, pressing, spray drying, extrusion, supercritical solvent extraction and tincture production. In cases where the herbal medicine is administered or sold in the form of a whole plant (or part thereof), the plant material may be dried prior to use. Any convenient form of drying may be used, including freeze-drying, spray drying or air-drying.

Compounds of the invention may be separated from the higher molecular weight components such as proteins and polysaccharides by extraction in polar solvents (such as ethanol/water mixtures, for example 250% v/v (e.g. up to ~70% v/v) ethanol/water mixtures). Other suitable techniques include various membrane technologies. These include microfiltration, ultrafiltration and nanofiltration. Alternatively, or in addition, electrodialysis may also be used to concentrate the charged compound. These methods use membranes of pore sizes that allow only molecules below a certain size to pass or rely on charges on the molecules to allow or not allow them to pass through the membrane. Anion and cation exchange resins may also be used to concentrate the compounds.

When isolated from a natural source, the compound for use according to the invention may be purified. In embodiments where the compound is formulated together with a pharmaceutically acceptable excipient, any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc.

The pharmaceutical compositions may take any suitable form, and include for example tablets, elixirs, capsules, solutions, suspensions, powders, granules and aerosols.

The pharmaceutical composition may take the form of a kit of parts, which kit may comprise the composition of the invention together with instructions for use and/or a plurality of different components in unit dosage form.

Tablets for oral use may include the compound for use according to the invention, mixed with pharmaceutically acceptable excipients, such as inert diluents, disintegrating agents, binding agents, lubricating agents, sweetening agents, flavouring agents, colouring agents and preservatives. Suitable Inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the compound for use according to the invention is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may Include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

For oral administration the compound or compounds can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch.

In another embodiment, the compounds of the invention are tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, colouring agents, and flavouring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The compounds of the invention may also be administered parenterally, that is, subcutaneously, intravenously, intramuscularly, or interperitoneally.

In such embodiments, the compound is provided as injectable doses in a physiologically acceptable diluent together with a pharmaceutical carrier (which can be a sterile liquid or mixture of liquids). Suitable liquids Include water, saline, aqueous dextrose and related sugar solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as poly(ethylene-glycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carhomers, methylcellulose, hydroxypropylmethylcellulose, or carboxymethylcellulose), or emulsifying agent and other pharmaceutically adjuvants. Suitable oils which can be used in the parenteral formulations of this invention are those of petroleum, animal, vegetable, or synthetic origin, for example, peanut oil, soybean oil, sesame oi, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate.

Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulphonates, alkyl, olefin, ether, and monoglyceride sulphates, and sulphosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the compound for use according to the invention in solution.

Preservatives and buffers may also be used. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compound or compounds for use according to the Invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers Topical formulations may contain a concentration of the compound from about 0.1 to about 10% w/v (weight per unit volume).

When used adjunctively, the compound or compounds for use according to the invention may be formulated for use with one or more other drug(s). Thus, adjunctive use may be reflected in a specific unit dosage designed to be compatible (or to synergize) with the other drug(s), or In formulations in which the compound or compounds are admixed with one or more enzymes. Adjunctive uses may also be reflected in the composition of the pharmaceutical kits of the invention, in which the compounds of the invention is co-packaged (e.g. as part of an array of unit doses) with the enzymes. Adjunctive use may also be reflected in information and/or instructions relating to the co-administration of the compound or compounds and/or enzyme.

Cosmetic Formulations

The cosmetic compositions of the invention may be selected for example from moisturizing compositions, cleansing compositions, or any composition that may provide a benefit to the skin. The cosmetic compositions of the invention may comprise cosmetically-acceptable excipients or carriers, for example selected from those described below.

In one embodiment, the cosmetic composition is a cleansing composition. Suitable cleansing compositions are solid or semi-solid at room temperature. Examples of useful cleansing compositions include, but are not limited to, fatty acid soaps, including glycerin soaps, synthetic detergents and mixtures thereof. Solid cleansing compositions are extensively taught in Soap Technology for the 1990's, the contents of which are incorporated herein by reference. It is desirable that the cleansing composition be flowable.

In one embodiment of the invention, the cleansing composition comprises glycerin soap. Examples of glycerin soaps useful in the present invention include but are not limited to those disclosed in U.S. Pat. Nos. 4,405,492 and 4,879,063, the disclosures of which are hereby Incorporated by reference.

Examples of suitable fatty acid soaps include soaps derived from hydrocarbon chain lengths of from approximately 10 to 22 (including carboxyl carbon) and may be saturated or unsaturated. The soap may be, for example, the sodium salt, potassium salt, ammonium salt, triethanolammonium salt and mixtures thereof.

Suitable synthetic detergents include those known in the art for the desired purpose. Examples of detergents useful for personal cleansing include the isethionates, sarcosinates, and glyceryl ether sulfonates which may be pure chain length variants or those derived from commercial oils such as coconut oil. Other suitable detergents include anionic acyl sarcosinates, methyl acyl taurates, N-acyl glutamates, alkyl sulphosuccinates, alkyl phosphate esters, ethoxylated alkyl phosphate esters, trideceth sulphates, protein condensates, mixtures of ethoxylated alkyl sulphates and alkyl amine oxides, betaines, sultaines and mixtures thereof. Included are the alkyl ether sulphates with 1 to 12 ethoxy groups, especially ammonium and sodium lauryl ether sulphates.

The cosmetic composition may be a moisturizing composition.

Other optional components of the cosmetic compositions of the invention include, but are not limited to, perfumes, fragrances, preservatives, colourants, dyes, anti-caking agents, and personal care ingredients, including, but are not limited to, skin and hair care ingredients.

Examples of suitable personal care ingredients useful in the present invention include but are not limited to safe and effective amounts of: humectants, sunscreen actives, skin soothers, anti-irritants, anti-inflammatories, emollients, conditioning agents, moisturizers, deodorants, anti-perspirants, artificial tanning agents, antimicrobial agents, anti-acne agents, anti-wrinkle agents, anti-skin atrophy agents, skin firming agents, anti-itch agents, anti-fungal agents, topical anaesthetics, skin tone evening agents, active natural ingredients, agents for minimizing the appearance or retarding regrowth of unwanted hair, skin texture modifiers, and additional cleansing agents.

In one embodiment the compound may be used from a water or alcoholic water extract by using a water in oil (w/o) emulsion such as are employed for example in the treatment of dry skin and emollient applications Emollients function by their ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 cetyl ether, steareth-10, oleth-8, PPG-4 lauryl ether, vitamin E acetate, PEG-7 glyceryl cocoate, lanolin, and combinations thereof. Vitamin E acetate, PEG-7 glyceryl cocoate and combinations thereof are preferred.

Examples of suitable humectants include polyhydric alcohols. Suitable polyhydric alcohols include, but are not limited to, glycerol (also known as glycerin), polyalkylene glycols, alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof.

Suitable skin soothers include, but are not limited to, panthenol, bisabolol, allantoin, aloe, and combinations thereof.

Suitable conditioning agents include, but are not limited to, dimethicone propyl PG-betaine, dimethicone copolyols, polyquaternium-10, guar, guar derivatives, and combinations thereof. Suitable anti-acne active ingredients include, but are not limited to, salicylic acid, sulphur, lactic acid, glycolic acid, pyruvic acid, urea, resorcinol, N-acetylcysteine, retinoic acid, benzoyl peroxide, octopirox, triclosan, azelaic acid, phenoxyethanol, phenoxypropanol, flavonoids, derivatives thereof, and combinations thereof. Salicylic acid and benzoyl peroxide are preferred.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1: Isolation and Identification of Compounds 1-3

The three 4-hydroxymethyl-N-methyl-L-prolines compounds (1-3) were all observed in fruit of *Z. jujuba*, Guarana seed and leaf of *Z. spina-christi* and have been isolated and the structures elucidated.

Guarana seed contained mainly compound 1 (approximately 0.1% w/w), along with smaller amounts of 2 and 3. The *Zizyphus* species were typically 2:1 ratios approximately of compound 1 and 3 respectively (approximately 0.1% w/w). Compounds 1 and 2 were isolated from *Z. jujuba* fruits and 3 from *Z. spina-christi.*

None of these compounds have been isolated from other sources.

*Zizyphus* Extract Preparation

A sample (200 g) of dry *Z. spina-christi* leaves (BEZ01) was extracted with 4 litres of 50% aqueous ethanol overnight. The filtered extract was passed down a cation exchange column (Amberlite IR120 in $H^+$ form) and the retained fraction was eluted with ammonia. This was then subjected to anion exchange column chromatography (Amberlite CG400 in $OH^-$ form) and the bound fraction was eluted with acetic acid and applied to a CG400 acetate-form column.

Analysis of the fractions allowed the identification of compounds 1 (HS0810/146/36-50 mg) and 3 (HS08101146/41-44 mg). Using the same method, compound 1 (JH0806/4214) and 2 (LJ746/18/7) were also isolated from fruits of *Z. jujuba* and 1 also from Guarana (JH0420/8/20).

Guarana extract (Blue Sky Botanics batch 150701A) was different from that of the *Zizyphus* species in having a major compound matching caffeine by GCMS of the trimethylsilyl-derivative (major ion 194 amu) at 9.9 minutes retention time under the GC conditions described below and also having a novel N-methylated pipecolic acid (N-methyl-4R,5S-dihydroxy-2S-pipecolic acid) (JH0806/90/5; retention time 8.4 minutes).

GC Analysis of Extracts and Pure Compounds

All samples were freeze dried before derivatisation. Trimethylsilyl (TMS) derivatives were prepared using a mixture of hexamethyldisilazane (HMDS) and trimethylchlorosilane (TMCS) in pyridine (Pierce 'Tri-Sil' silylation reagent, HMDS:TMCS:pyridine in a ratio of 2:1:10). Samples were heated at 60° C. for 15 minutes and then left at room temperature for at least 60 min. Insoluble reaction products were sedimented by centrifugation, and the supernatant was transferred to fresh vials using a syringe.

Analysis was carried out by GC-MS using a Perkin Elmer Autosystem XL gas chromatograph with a high polarity fused-silica column (Varian 'Factor Four' VF-5 ms column, 25 m×0.25 mm id., 0.25 mm phase thickness). The carrier gas (helium) flow rate was 1 ml/min. Trimethylsilyl—(TMS) derivatives were separated using a temperature programme that started at 160° C. for 5 min, followed by a linear increase to 300° C. at a rate of 10° C./min. The temperature was held at 300° C. for an additional 10 min; the total analysis time was 29 min. Electron impact mass spectrometry of the column eluant was carried out using a Perkin Elmer TurboMass Gold mass spectrometer, with a quadrupole ion filter system, which was run at 250° C. constantly during analysis. The detector mass range was set to 100 to 650 amu. The temperature of the transfer line (GC to MS) was held at 250° C. Samples were injected onto the column via a split vent (split ratio 50:1) through a fused silica narrow bore injection liner packed with deactivated quartz wool: the injection port temperature was maintained at 200° C. The injection volume was 1 μl. System control, data collection and mass spectral analysis was carried out using Perkin Elmer TurboMass software (TurboMass v. 4.4).

The compounds 1-3 give distinctive mass spectra as the trimethylsilyl-derivatives prepared as above with different retention times by GCMS under conditions described.

Compound 1, distinctive ions 186 (100%), 260 (10%) and 288 (10%) amu (retention time 4.8 minutes).

Compound 2, distinctive ions 170 (10%) and 188 (100%) amu (retention time 5.6 minutes).

Compound 3, distinctive ions 170 (10%), 274 (100%), 288 (15%) and 376 (10%) amu (retention time 7 minutes).

Determination of Structures

Compounds purified by ion exchange were analysed on a Bruker Avance 500 MHz instrument with deuterium oxide as the solvent. The NMR elucidation is described below.

Structural Elucidation of Compound 1

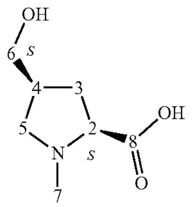

| No. | C shift/ppm | H shift/ ppm | No. H's | multiplicity | Coupling, J/Hz | ppm range |
|---|---|---|---|---|---|---|
| 2 | 71.2 | 3.89 | 1 | t | 9.14 | 3.86-3.93 |
| 3 | 32.2 | 1.77 | 1 | m | — | 1.71-1.82 |
| | | 2.60 | 1 | dt | 13.6, 8.4 | 2.55-2.65 |
| 4 | 38.6 | 2.70 | 1 | m | — | 2.65-2.77 |
| 5 | 58.2 | 3.29 | 1 | dd | 12.0, 8.8 | 3.24-3.34 |
| | | 3.52 | 1 | m | — | 3.48-3.58 |
| 6 | 62.8 | 3.50 | 2 | m | — | 3.46-3.50 |
| 7 | 41.4 | 2.87 | 3 | s | — | 2.87 |
| 8 | 173.6 | — | — | q | — | — |

$^1$H NMR (500 MHz, $D_2O$) δ/ppm 3.89 (1H, t, J=9.14 Hz, 2), 3.48-3.58 (2H, m, 5), 3.46-3.50 (1H, m, 6), 3.29 (1H, dd, J=12.0, 8.8 Hz, 5), 2.87 (3H, s, 7), 2.65-2.77 (1H, m, 4), 2.60 (1H, dt, J=13.6, 8.4 Hz, 3), 1.71-1.82 (1H, m, 3)

$^{13}$C NMR (126 MHz, $D_2O$) δ/ppm 173.6 (8), 71.2 (2), 62.8 (6), 58.2 (5), 41.4 (7), 38.6 (4), 32.2 (3)

Proton attachment to individual carbon atoms were assigned from pendant and HMQC spectra. COSY correlations show linkages from 2 to 3 to 4, and correlations from 4 to both 5 and 6. The hydrogen chemical shifts of the CH at δ 3.89 ppm (2), the methyl at δ 2.87 ppm (7) and the methylene at δ 3.29 ppm and δ 3.52 ppm (δ) indicates all to be attached to nitrogen thus forming a N-methyl-pyrrolidine ring structure.

The hydrogen chemical shift of the methylene at δ 3.50 ppm (δ) indicates it to be attached to a hydroxyl, thus forming a hydroxylmethyl attached to 4. HMBC correlations from 2 and 3 to the quaternary at δ 173.6 ppm indicate an acid to be attached to 2.

NOESY correlations between protons at δ 3.89 ppm (2) and δ 2.70 ppm (4) indicate them to be on the same side of the ring thus giving an S, S configuration. Based on these interpretations the structure is postulated to be N-methyl-4S-(hydroxymethyl)-2S-pyrrolidinecarboxylic acid (Compound 1).

The chemical shifts of the protons are in good agreement with those expected from standard tables of substituent effects, and the carbon shifts match closely the predicted values (ACD CNMR predictor). The structure elucidated has not been previously reported.

Structural Elucidation of Compound 2

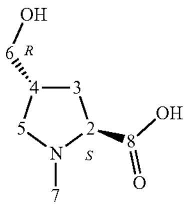

| No. | C shift/ppm | H shift/ ppm | No. H's | multiplicity | Coupling, J/Hz | ppm range |
|---|---|---|---|---|---|---|
| 2 | 68.6 | 3.01 | 1 | m | — | 2.96-3.05 |
| 3 | 33.2 | 1.46 | 1 | dt | 8.8, 4.7 | 1.38-1.52 |
| | | 2.29 | 1 | m | — | 2.22-2.29 |
| 4 | 38.6 | 2.34 | 1 | m | — | 2.29-2.42 |
| 5 | 57.8 | 2.91 | 1 | d | 10.7 | 2.36-2.95 |
| | | 2.51 | 1 | m | — | 2.44-2.57 |
| 6 | 64.5 | 3.47 | 2 | m | — | 3.39-3.53 |
| 7 | 41.4 | 2.22 | 3 | s | — | 2.22 |
| 8 | 173.6 | — | — | q | — | — |

$^1$H NMR (500 MHz, $D_2O$) δ/ppm 3.39-3.53 (2H, m, 6), 2.96-3.05 (1H, m, 2), 2.91 (1H, d, J=10.7 Hz, 5), 2.42-2.57 (1H, m, 5), 2.29-2.42 (1H, m, 4), 2.22-2.29 (1H, m, 3), 2.22 (3H, s, 7), 1.46 (1H, dt, J=8.8, 4.7 Hz, 3).

$^{13}$C NMR (126 MHz, $D_2O$) δ/ppm 173.6 (8), 68.6 (2), 64.5 (6), 57.8 (5), 41.4 (7), 38.6 (4), 33.2 (3)

Proton attachment to individual carbon atoms were assigned from pendant and HMQC spectra. COSY correlations show linkages from 2 to 3 to 4, and correlations from 4 to both 5 and 6. The hydrogen chemical shifts of the CH at δ 3.01 ppm (2), the methyl at δ 2.22 ppm (7) and the methylene at δ 2.91 ppm and δ 2.51 ppm (δ) indicates all to be attached to nitrogen thus forming a N-methyl-pyrrolidine ring structure. The hydrogen chemical shift of the methylene at δ 3.47 ppm (δ) indicates it to be attached to a hydroxyl, thus forming a hydroxylmethyl attached to 4. HMBC correlations from 7 to 2 and 5 confirm the N-methylpyrrolidine ring structure. HMBC correlations from 2 and 3 to the quaternary at δ 173.6 ppm indicate an acid to be attached to 2. There are no NOESY correlations between protons at δ 3.01 ppm (2) and δ 2.34 ppm (4) Indicating them to be on opposite sides of the ring thus giving a S, R configuration. Based on these interpretations the structure is postulated to be N-methyl-4R-(hydroxymethyl)-2S-pyrrolidinecarboxylic acid (Compound 2).

The chemical shifts of the protons are in good agreement with those expected from standard tables of substituent effects, and the carbon shifts match closely the predicted values (ACD CNMR predictor).

The structure elucidated has not been previously reported.

Structural Elucidation of Compound 3

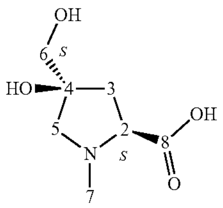

| No. | C shift/ppm | H shift/ ppm | No. H's | multi- plicity | Coupling, J/Hz | ppm range |
|---|---|---|---|---|---|---|
| 2 | 70.6 | 4.21 | 1 | dd | 11.3, 7.3 | 4.17-4.24 |
| 3 | 39.4 | 2.13 | 1 | dd | 13.9, 11.3 | 2.08-2.17 |
| | | 2.41 | 1 | dd | 13.9, 7.3 | 2.37-2.45 |
| 4 | 79.9 | — | — | q | — | — |
| 5 | 63.3 | 3.14 | 1 | d | 12.9 | 3.11-3.17 |
| | | 3.81 | 1 | d | 12.9 | 3.78-3.84 |
| 6 | 64.9 | 3.58 | 2 | s | — | 3.58 |
| 7 | 43.1 | 2.99 | 3 | s | — | 2.99 |
| 8 | 172.8 | — | — | q | — | — |

$^{1}$H NMR (500 MHz, $D_2O$) δ/ppm 4.21 (1H, dd, J=11.3, 7.3 Hz, 2), 3.81 (1H, d, J=12.9 Hz, 5), 3.58 (2H, s, 6), 3.14 (1H, d, J=12.9 Hz, 5), 2.99 (3H, s, 7), 2.41 (1H, dd, J=13.9, 7.3 Hz, 3), 2.13 (1H, dd, J=13.9, 11.3 Hz, 3)

$^{13}$C NMR (126 MHz, $D_2O$) δ/ppm 172.8 (8), 79.9 (4), 70.6 (2), 64.9 (6), 63.3 (5), 43.1 (7), 39.4 (3)

Proton attachment to individual carbon atoms were assigned from pendant and HMQC spectra. COSY correlations show linkages from 2 to 3. The hydrogen chemical shifts of the CH at δ 4.21 ppm (2), the methyl at δ 2.99 ppm (7) and the methylene at δ 3.14 ppm and δ 3.81 ppm (δ) indicates all to be attached to nitrogen thus forming a N-methyl ring structure. HMBC correlations from the methyl at δ 2.99 ppm (7) to 2 and 5 confirm this arrangement. The singlet at δ 3.58 ppm integrates as two protons implying a hydroxymethyl from the carbon and hydrogen chemical shifts. This gives HMBC correlations to 3, 4 and 5. The fact that it is a singlet implies it is attached to a quaternary, therefore 4. The carbon chemical shift of 4 implies it has a hydroxyl unit attached.

Based on these interpretations the structure is postulated to be N-methyl-4-hydroxy-4-(hydroxymethyl)-2-pyrrolidinecarboxylic acid. There is a NOESY correlation between 2 and 6 implying the hydroxymethyl is on the same side of the ring as the proton thus postulating the structure to be N-methyl-4-hydroxy-4S-(hydroxymethyl)-2S-pyrrolidinecarboxylic acid (compound 3).

The chemical shifts of the protons are in good agreement with those expected from standard tables of substituent effects, and the carbon shifts match closely the predicted values (ACD CNMR predictor). The structure elucidated has not been previously reported.

Comparison with the proton spectra for Compound 1 and Compound 3 with the proton NMR spectrum of an extract of *Z. spina-christi* (NMR file K101613) confirmed it to contain a mixture of the two compounds as the major N-methylproline components along with amino acids.

Example 2: Disaccharide Loading Tests in Mice Using Compounds 1 and 3 and *Z. spina-christi* Extract Introduction Purified compounds 1 and 3 were studied for their blood sugar regulating activities in mice along with an extract of *Z. spina-christi* containing both compounds.

Method

The animal experimental protocols in this study were approved by the Animal Experiments Committee of the University of Toyama (S-2010 UH-2). Male ddy mice (29-33 g) after an overnight fast were used for acute disaccharide loading tests. Maltose (2.5 g/kg body weight) or Sucrose (2.5 g/kg body weight) as well as the test samples were dissolved in 0.9% NaCl solution and administered to mice via a stomach tube. A control group was loaded with saline only.

Blood samples for glucose measurements were obtained from the tail vein at 0, 15, 30, 60, and 120 min after disaccharide-loading. The blood glucose levels were measured by a portable kit, Antsence II™ (Sankyo Co. Ltd. Tokyo. Japan). The *Zizyphus* extract HS0810/142/41 as well as the purified compounds were tested in this way.

TABLE 1

Effect of *Zizyphus* extract on Blood Glucose Levels. Blood glucose concentrations of male ddy mouse after an oral load with maltose, 2.5 g/kg body weight, with 500 mg/kg body weight of *Zizyphus* or with saline. Each value represents the mean (n = 5).

| Time after Administration (min) | *Zizyphus* effect on blood glucose(mg/dL) | Control blood glucose(mg/dL) |
|---|---|---|
| 0 | 68 | 79 |
| 15 | 228 | 274 |
| 30 | 178 | 210 |
| 60 | 114 | 117 |
| 120 | 71 | 81 |

TABLE 2

Effects of Compound 1 on Blood Glucose Levels. Blood glucose concentrations of male ddy mouse after an oral load with maltose, 2.5 g/kg body weight, with 500 mg/kg body weight of Compound 1 or with saline. Each value represents the mean (n = 5).

| Time after Administration (min) | Compound 1 effect on blood glucose(mg/dL) | Control blood glucose(mg/dL) |
|---|---|---|
| 0 | 83 | 72 |
| 15 | 231 | 267 |
| 30 | 187 | 229 |
| 60 | 140 | 117 |
| 120 | 74 | 70 |

TABLE 3

Effects of Compound 3 on Blood Glucose Levels. Blood glucose concentrations of male ddy mouse after an oral load with maltose. 2.5 g/kg body weight, with 500 mg/kg body weight of Compound 3 or with saline. Each value represents the mean (n = 5).

| Time after Administration (min) | Compound 3 effect on blood glucose(mg/dL) | Control blood glucose(mg/dL) |
|---|---|---|
| 0 | 83 | 66 |
| 15 | 233 | 237 |
| 30 | 185 | 215 |
| 60 | 130 | 126 |
| 120 | 80 | 65 |

TABLE 4

Effects of Compound 3 and DMDP on Blood Glucose Levels. Blood glucose concentrations of male ddy mouse after an oral load with sucrose, 2.5 g/kg body weight, with 500 mg/kg body weight of Compound 3 or 500 mg/kg body weight of DMDP (glucosidase inhibitor) or with saline. Each value represents the mean (n = 5).

| Time after Administration (min) | Compound 3 effect on blood glucose(mg/dL) | DMDP effect on blood glucose(mg/dL) | Control blood glucose(mg/dL) |
|---|---|---|---|
| 0 | 109 | 98 | 88 |
| 15 | 183 | 115 | 162 |
| 30 | 143 | 100 | 149 |
| 60 | 106 | 88 | 120 |
| 120 | 80 | 53 | 60 |

Conclusion

The *Zizyphus* mixture had a lowering effect on blood glucose levels following disaccharide challenge with maltose as did Compound 1. Compound 3 seemed to have a more complex effect with a faster drop at 30 minutes but an apparent increase in blood glucose early on in the sucrose challenge but falling below the higher starting point than the other groups by 2 hours indicating perhaps better regulation than with DMDP and the controls where blood glucose fell lower.

Example 3: Lack of Glucosidase Inhibition by Compounds 1 and 3

Introduction

Glycosidase assays were conducted on Compounds 1 and 3 and an extract of *Zizyphus* used in the disaccharide loading mouse studies to determine if glucosidase inhibition might explain the effects on blood glucose. A panel of glycosidases were used to be sure any activity found was a selective inhibition and not just non-specific binding to the enzyme.

Enzyme Assays

Glycosidase assays were conducted as described by Watson et al. (Phytochemistry 1997, 46, 255) using p-nitrophenyl-substrates (except sialidase which used methylumbelliferyl-N-acetylneuraminic acid as substrate). Assays were carried out in microtitre plates. Enzymes were assayed in 0.1 M citric acid/0.2 M di-sodium hydrogen phosphate (McIlvaine) buffers at the optimum pH for the enzyme. All assays were carried out at 20° C. All enzymes and substrates were purchased from Sigma Aldrich Chemicals Limited. The incubation mixture consisted of 10 μl of enzyme solution, 10 μl of the iminosugars solution and 50 μl of the appropriate 5 mM p-nitrophenyl substrate made up in McIlvaine buffer at the optimum pH for the enzyme. The reactions were stopped with 0.4 M glycine (pH 10.4) during the exponential phase of the reaction. Absorbances were read at 405 nm. Water was substituted for the alkaloids in the blanks. Reactions were carried out in triplicate.

Enzyme inhibitor solutions—Compounds were dissolved in distilled water at a concentration of 1 mg $mL^{-1}$ and then screened at a concentration of 0.14 mg $mL^{-1}$ after dilution of the 1 mg $mL^{-1}$ in the assay volumes of substrates.

Sialidase assays used 1 mM inhibitor (or water without inhibitor) and 2.5 nM sialidase (including NanH from *T. forsythia*) incubated in the presence of 0.1 mM methylumbeliferyl-N-acetylneuraminic acid, pH 7.2 in 20 mM sodium phosphate buffer. Reactions were stopped at 30 seconds and 60 seconds via addition of ph 10.5 60 mM sodium carbonate buffer. Release of fluorogenic MU was quantified by measuring fluorescence emission at 450 nm, excitation 350 nm. Percentage sialidase activity was expressed as the change in fluorescence between 30 seconds and 60 seconds compared to that of a reaction without inhibitor. Reactions were carried out in triplicate.

Results

The results are expressed as % inhibition. No glucosidase inhibition was observed for the *Zizyphus* extract or the Compound 1 and 3 from *Zizyphus* and Guarana. The glucosidase inhibitors DMDP and DNJ (1-deoxynojirimycin) showed the expected strong inhibition of various glucosidases. Of the other glycosidases tested the only inhibition seen with the Isolated compound was with sialidase from the bacterium *T. forsythia* with Compound 1 (Compound 3 and the *Zizyphus* extract were not available for that assay).

| Enzyme | Source | *Zizyphus* extract HS081D/142/41 | Cmpd 1 | Cmpd 3 | DMDP | DNJ |
|---|---|---|---|---|---|---|
| α-D-glucosidase | *Saccharomyces cerevisiae* | 6 | <5 | <5 | **97.37** | 35.67 |
| α-D-glucosidase | *Bacillus sterothermphilus* | −55 | 22 | 13 | **92.98** | **99.48** |
| α-D-glucosidase | Rice | 6 | 5 | 11 | **94.59** | **99.56** |
| β-D-glucosidase | Almond | −10 | 15 | <5 | **96.61** | 63.7 |
| α-D-galactosidase | Green coffee bean | −18 | <5 | <5 | 6.95 | −3.34 |
| β-D-galactosidase | Bovine liver | 19 | <5 | <5 | **98.75** | 0.45 |
| α-L-fucosidase | Bovine kidney | ND | 15 | ND | 4.84 | 5.86 |
| α-D-mannosidase | Jack bean | −28 | 18 | 6 | 2.70 | 26.65 |
| β-D-mannosidase | *Cellullomonas fimi* | −8 | <5 | <5 | **93.34** | −19.03 |
| Naringinase | *Penicillium decumbens* | ND | 11 | ND | 2.97 | 20.81 |
| N-acetyl-β-D-glucosaminidase | Bovine kidney | −15 | <5 | <5 | −7.60 | −0.83 |

-continued

| Enzyme | Source | *Zizyphus* extract HS081D/142/41 | Cmpd 1 | Cmpd 3 | DMDP | DNJ |
|---|---|---|---|---|---|---|
| N-acetyl-β-D-glucosaminidase | Jack bean | ND | <5 | −5 | −6.65 | 2.76 |
| N-acetyl-β-D-hexosaminidase | *Aspergillus oryzae* | ND | −6 | −6 | 5.62 | −5.50 |
| Amyloglucosidase | *Aspergillus niger* | ND | ND | ND | 46.84 | 31.71 |
| β-D-glucuronidase | Bovine liver | 5 | <5 | −5 | ND | ND |
| sialidase | *Tannerella forsythia* | ND | **50** | ND | −2 | 2 |

ND = not determined.

Numbers in bold show strong inhibition at the concentration tested 0.4 mM

Negative values indicate an increased enzyme activity perhaps by stabilisation or improved folding DMDP and DNJ are the most commonly occurring plant iminosugars and both are strong inhibitors of alpha-glucosidases (Watson, A. A., Fleet, G. W. J., Asano, N., Molyneux, R. J.; Nash, R. J. *Phytochemistry* 2001, 56, 265-295). DNJ (1-deoxynojirimycin), first isolated from Mulberry, used for diabetes in Chinese traditional medicine.

Example 4: Reduction of TNF-α by Compound 1

Introduction

The measurement of TNF-α production in human blood is predictive of the actions of any agents administered systemically on TNF-α levels i.e. the effects in blood either ex vivo or in vitro precisely mimic those in vivo. This is especially useful when it is difficult to carry out studies directly in humans in vivo for either ethical concerns or more importantly safety considerations. Whole blood incubations have been shown to be useful to demonstrate stimulation of pro-inflammatory mediators in vitro in humans (Finch-Arietta, M. B. & Cochran, F. R., 1991, Agents and Actions 34, 49). This approach is also useful for monitoring the bioavailability of any agents administered systemically (Song, H. J. et al., 2005, European Journal of Clinical Nutrition 59, 508).

There are several approaches to suppressing Inflammation, the two most routinely used therapeutically at present are a) steroids (glucocortincoid analogues) and b) agents that neutralise the actions of TNF-α such as etanercept (soluble TNF-α receptor fusion protein) and infliximab (monoclonal antibody to TNF-α). Both these approaches target pro-inflammatory cytokines, suppression of production by steroids and preventing the actions of TNF-α by etanercept and infliximab. This also demonstrates the importance of targeting TNF-α to suppress inflammatory responses (Feldmann, M. & Maini, R. N., 2001, Annual Review of Immunology 19, 163). Similarly, glucocorticoid analogues also suppress the production of cytokines and dexamethasone, and specifically, can reduce the LPS-stimulated production of TNF-α from human monocytes (Waage, A. & Bakke, O., 1988, Immunology 63: 299).

The aim of this study was to evaluate the anti-inflammatory activity of Compound 1 with respect to the ability to modulate TNF-α levels in whole human blood.

Materials

Blood and buffy coat fractions were supplied by the Scottish National Blood Transfusion Service (SNBTS), Glasgow, UK. Ficoll Histopaque (1.077 g/l). Lipopolysaccharide (from *Salmonella abortus equi*) was purchased from Sigma-Aldrich Co. Ltd. (UK). PGE was from Cayman Chemical Co. (Ann Arbor, MI). Human TNF-α antibody pairs for TNF-α ELISA assays was from Invitrogen/Life Sciences Europe. All drugs were dissolved in RPMI 1640 medium from Gibco BRL, UK.

Methods

In the experiments with whole blood incubations, blood was used without any further treatment following donation. Blood was kindly supplied by the Scottish National Blood Transfusion Service from normal healthy donors as defined by ensuring they all tested negative for HIV, hepatitis B & C, CMV and parasitic diseases such as malaria (as tested by the National Blood Transfusion service). They were also confirmed by our laboratory to be free of acute inflammatory disease at the time the blood was taken by measuring the basal level of TNF-α which was always <50 pg/ml.

Stimulation of Cells and Measurement of TNF-α

Aliquots (800 μl) of whole blood were incubated with the compound dissolved in RPMI 1640, as indicated in the results, for the appropriate preincubation period after which LPS was added and incubations continued for a further 20 hr at 37° C. in a humidified (100%) atmosphere of 5% CO2 In air. At the end of the Incubation period, supernatants consisting from either plasma or culture medium were collected by centrifugation at 10,000 g for 30 seconds at room temperature and TNF-α levels measured using a human TNF-α, ELISA system (BioSource Europe S.A., Belgium, supplied by Invitrogen), according to the manufacturers instructions as described previously (Brown et al., 2013).

Results and Conclusions

Compound 1 showed a mean value trend towards reducing the production of LPS-stimulated TNF-α in a concentration-dependent manner in human blood.

Figure 1:
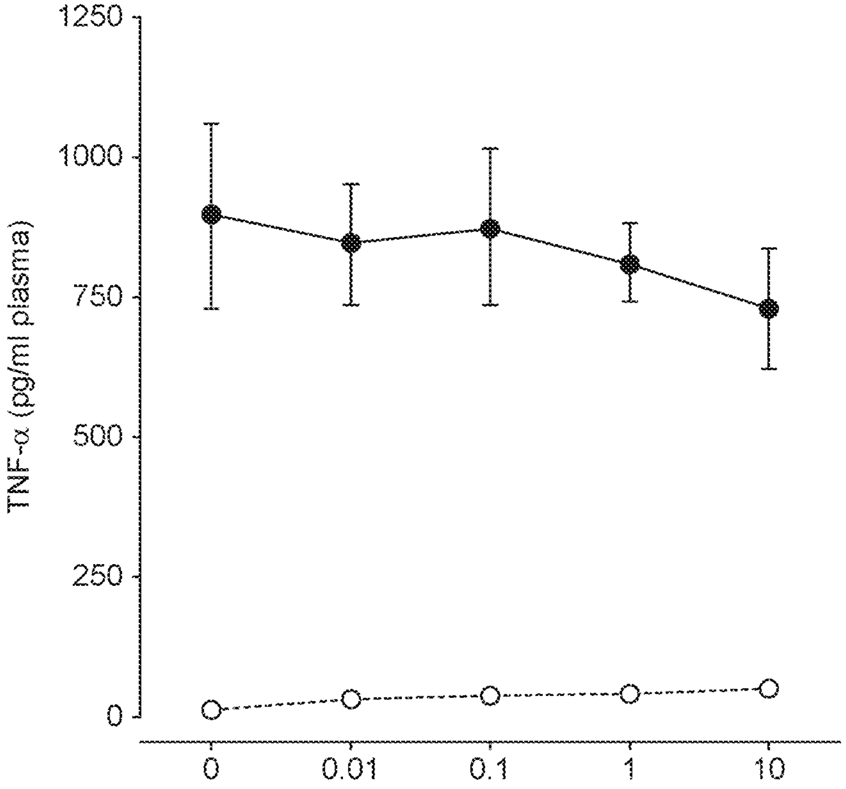
FIG. 1 shows the effect of compound 1 (μM) on LPS-stimulated TNF-α production in human blood. Whole blood was incubated for 24 h in the absence (open symbols) or presence (filled circles) of LPS (10 μg/ml) with varying concentrations of the compound.

FIG. 1 shows the effect of compound 1 (μM) on LPS-stimulated TNF-α production in human blood. Whole blood was incubated for 24 h in the absence (open symbols) or presence (filled circles) of LPS (10 μg/ml) with varying concentrations of the compound. Following incubation at 37° C. (5% $CO_2$, 100% humidity) plasma was collected from blood by centrifugation and the levels of TNF-α in plasma samples were measured by ELISA. Values represent the means±s.d. of n=3.

Although not significant at the low μM concentrations used here the concentration in the *Zizyphus* plant extracts may be high depending on how they are produced and this and the other 4-hydroxymethyl-N-methyl-L-prolines (compounds 1, 2 and 3) may help to explain the anti-inflammatory activity claimed for the plant.

Example 5: Effects of 4-hydroxymethyl-N-methyl-L-prolines on Sialidases and Growth of Periodontal Pathogens Periodontal disease is a significant health burden with an estimated 700 million sufferers worldwide and affecting approximately 10-20% of the UK population. In addition to being a cause of tooth loss, recent studies have shown that increased incidence of periodontal disease is associated with a range of important systemic diseases, such as cardiovascular disease, diabetes and rheumatoid arthritis. It shows increased incidence with age.

As part of disease progression the ability of periodontal bacteria to form sub-gingival plaque biofilms and their ability to stimulate innate immunity via interactions with oral epithelial cells are considered key to pathogenesis. Pathogen sialidases from the periodontal pathogens *Tannerella forsythia, T. denticola* and *Porphyromonas gingivalis* have been shown to be involved in this process. Thus, sialidase inhibition represents a possible treatment or preventative for periodontitis. Related enzymes exist as major virulence factors of influenza virus (i.e. the N In H1N1 represents neuraminidase, the target of TamiFlu).

The aim of this study was to investigate the ability of the 4-hydroxymethyl-N-methyl-L-prolines to inhibit sialidase activity of periodontal bacteria and their purified sialidases and 30 also the effects of extracts containing the compounds (e.g. *Zizyphus* fruit). In addition, preliminary studies on in vitro models of biofilm formation and host-bacteria association were performed to assess the impact of the compounds and extracts on virulence of periodontal pathogens, since these are considered important to pathogen survival and proliferation in the oral cavity.

Effects in these assays may also indicate influences of the compounds and extracts containing them on the human microbiome more generally with possible links to prevention or cure of other disease states in which sialidase activity is implicated.

Sialidase Activity Assays

In these assays a fluorogenic substrate Methylumbelliferyl-N-Acetylneuraminic Acid (MUNANA) was used which is cleaved via the action of sialidases to release N-Acetylneuraminic Acid (Neu5Ac) and methylumbelliferone (MU), the latter shows maximum fluorescence at 450 nm on excitation at 350 nm. MU release can be used to quantify sialidase activity.

Whole bacteria or purified sialidases were exposed to MUNANA, in the presence or absence of compound 1 (Example 3) or *Zizyphus* fruit 50% aqueous ethanol extract containing 1% of the N-methyl-prolines.

1 mM inhibitor (or water without inhibitor) and 2.5 nM sialidase (including NanH from *T. forsythia*) was incubated in the presence of 0.1 mM MUNANA. pH 7.2 20 mM Sodium Phosphate buffer. Reactions were stopped at 30 seconds and 60 seconds via addition of ph 10.5 60 mM sodium carbonate buffer. Release of fluorogenic MU was quantified by measuring fluorescence emission at 450 nm, excitation 350 nm. Percentage sialidase activity was expressed as the change in fluorescence between 30 seconds and 60 seconds compared to that of a reaction without inhibitor. Reactions were carried out in triplicate.

An initial screen of N1Neu inhibition using a variety of compounds and the commercially available sialidase (neuraminidase) inhibitor Zanamivir (which is sold in the pharmaceutical preparation "Relenza™" as a treatment for flu) was performed.

Initial Screen of Compounds and Plant Extracts on Neu1 Activity

Sialidase assays were performed, reactions contained 0.1 mM MUNANA, pH 7.4 50 mM Tris, 5 mM CaCl2), 200 mM NaCl, plant extract or the control sialidase inhibitor Zanamivir at the concentrations indicated, or no putative inhibitor. N1Neu was present at 0.025 μg/ml in reactions. 50 μl of these reactions were quenched using 100 μl of 100 mM sodium carbonate buffer, pH 10.5, at 5 minutes and 10 minutes. The 10 minute time point was used to assess sialidase activity. Data shown represent the mean of one experiment, where each condition was repeated in triplicate. MU present in quenched reactions was quantified using TECAN M200 Infinite microplate reader at excitation 340 nm emission 430 nm, and expressed as the percentage of sialidase activity (MU fluorescence) relative to the no inhibitor condition.

Host Cell Association

In addition to forming biofilms and existing at the mucosal surface, bacteria can associate with (attach to and invade) host cells. This has several benefits for bacteria, including persistence in the face of antimicrobial therapy, the immune system, or mechanical removal of the biofilm, and access to nutrients within the host cell. Bacterial association with host cells also has consequences for immunoregulation, i.e. increased cellular Invasion may lead to upregulation of Inflammation and contribute to periodontal disease. Sialidases (and other products) are important during *P. gingivalis* and *T. forsythia* association with host cells.

To test for inhibition of attachment and invasion of host cells by *P. gingivalis* and *T. forsythia* antibiotic protection assays were used. These involved growing two sets of host cell monolayers, which were then infected with bacteria at a ratio (multiplicity of infection) of 1:100 host cells:bacteria. After an incubation for 1.5 hours, one set was lysed and the bacteria plated out on agar to obtain the number of viable bacteria; this gives the total associated number of bacteria. The second set of infected monolayers was incubated for one hour with an antibiotic, Metronidazole, which kills any external (attached) bacteria, leaving only the invaded (internalised) bacteria, cells were then lysed and plated out on agar as above, and the number of invaded bacteria subtracted from total associated to obtain attached (external) bacteria.

Biofilm Assays

Periodontal pathogens exist in a biofilm in the oral cavity (as part of the plaque), and both normal oral hygiene methods and periodontitis therapy is to disrupt the biofilm. Therefore, any potential therapeutic or preventative should also be capable of disrupting periodontal pathogen biofilms, which can be modelled in vitro as single or mixed species biofilms. Since the effect of plant extracts and compounds may not be directly antimicrobial, but act to prevent attachment to host glycoproteins, or prevent nutrient acquisition from glycoproteins, a variety of different approaches were taken. These involved culturing *P. gingivalis* and *T. forsythia* on serum (foetal bovine serum-FBS) coated surfaces in nutrient rich media (tryptic soy broth-TSB), and *P. gingivalis* in nutrient deficient media, containing only serum (10% v/v FBS) as a carbon and nitrogen source. Given the apparent activity as sialidase inhibitors, the extract from *Zizyphus* was tested for its ability to prevent biofilm formation.

Two approaches were used to quantify biofilm formation, crystal violet staining, which is high throughput but with lower sensitivity, and direct bacterial counting, which has higher sensitivity but lower throughput than crystal violet staining. Crystal violet staining could also be used to image the biofilms for qualitative observations.

*P. gingivalis* and *T. forsythia* were cultured in supplemented TSB for 2 and 5 days, respectively, in microtitre plates pre-coated with FBS, in the presence or absence of 1500 μg/ml *Zizyphus* extract. For this set of experiments, bacterial counting enabled quantification of biofilm formation, while crystal violet staining allowed visualisation of biofilms. Under these conditions. *P. gingivalis* biofilm formation was not significantly inhibited. *T. forsythia* biofilm formation was reduced by at least twofold in all of the conditions, from $2.2\times10^7$ bacteria/ml in the no inhibitor control, to $1.0\times10^7$.

Biofilm Inhibition Assays—*P. gingivalis*+*F. nucleatum* (25586) Mixed Species Biofilm in Rich Media The Effect of *Zizyphus* Extract on *T. forsythia* and *P. gingivalis* Cultured in TSB on Serum Coated Surfaces

*P. gingivalis* or *T. forsythia* were inoculated at an OD600 of 0.05 into TSB containing 0.1% w/v yeast extract, 5 μg/ml hemin. 1 μg/ml menadione, and 50 μg/ml gentamicin, in the wells of a 96 well poly-lysine coated tissue culture plate which had been pre-coated with FBS (50 μl of 100% FBS added and incubated overnight at 4° C. then washed once with PBS to remove unbound serum). Both species were incubated anaerobically at 37° C., *T. forsythia* for 5 days, *P. gingivalis* for 48 hours. Supernatant was removed, and wells washed twice with PBS. Biofilms were vigorously resuspended in PBS before dilution (where appropriate), and counting using a helber chamber and phase contrast microscopy at 400× magnification.

Wells for imaging were stained by crystal violet; supernatant was removed, and wells incubated with 0.1% (w/v) crystal violet for 15 minutes at room temperature, stain was removed, and wells washed three times using PBS. Biofilms were imaged at 400× magnification using an inverted microscope and imaging software. Image capture parameters (light intensity and exposure time) were constant for each image. Data shown represent the mean of three experiments, where each condition was repeated three times per experiment.

A possible explanation for the different effects of the *Zizyphus* extract on biofilm formation is the difference in nutritional requirements of these two organisms, *T. forsythia* has more fastidious growth requirements than *P. gingivalis*. For example, *T. forsythia* usually requires an exogenous source of N-acetylneuraminic acid (NAM), though this can be substituted with sialic acid during biofilm formation (In this experiment this source was provided by FBS), and this could be disrupted by sialidase inhibition, whereas *P. gingivalis* might be able to obtain its nutritional requirements from the supplemented TSB culture medium, even in the presence of sialidase inhibition. Therefore, a defined media containing only serum (FBS) as a carbon and nitrogen source was also utilised to assess the effect of the *Zizyphus* extract on biofilm formation Biofilm Inhibition Assays—*P. gingivalis* in Defined Media

*T. forsythia* is more fastidious than *P. gingivalis*, and efforts to culture it as a single species biofilm using the defined media was unsuccessful. We therefore tested *Zizyphus* extract just on *P. gingivalis* cultured in defined media. *P. gingivalis* was Inoculated at an OD600 of 0.05 into a defined media which was further supplemented with 10% v/v FBS, 5 μg/ml hemin, 50 μg/ml gentamicin, in the wells of a 96 well poly-lysine coated tissue culture plate which had been pre-coated with FBS (50 μl of 100% FBS added and incubated overnight at 4° C., then washed once with PBS to remove unbound serum). *P. gingivalis* was Incubated anaerobically at 37° C. for 5 days.

Supernatant was removed, and wells incubated with 0.1% (w/v) crystal violet for 15 minutes at room temperature. Stain was removed, and wells washed by water flow. A) Quantification of crystal violet staining-crystal violet was extracted from biofilms using ethanol:acetone (80:20) into a fresh 96 well microtitre plate and quantified by measuring absorbance at 590 nm.

Results

Data shown represent the mean of two experiments, where each condition was repeated ten times per experiment.

N1 Neu Sialidase Inhibition

*Zizyphus* was capable of reducing N1 Neu activity, from 100% to 34% (p=<0.05)

| Material | % inhibition |
|---|---|
| 2 mM Zanamivir | 100 |
| 1500 μg *Zizyphus* extract | 66 |
| Control | 0 |

Sialidase Activity of Homogenate of *T. forsythia*

| Material | % inhibition |
|---|---|
| 2 mM Zanamivir | 22 |
| 1500 μg/ml *Zizyphus* | 44 |
| Control | 0 |

N.B. Compound 1 at 1 mM gave 50% inhibition of NanH from *T. forsythia* (Example 3)

Sialidase Activity of Homogenate of *P. gingivalis*

| Material | % inhibition |
|---|---|
| 2 mM Zanamivir | 51 |
| 1500 μg/ml *Zizyphus* | 24 |
| Control | 0 |

Host Cell Association: Antibiotic Protection Assay Showing % Viability of *T. forsythia*

| Material | attachment | invasion | Total association |
|---|---|---|---|
| 1500 μg/ml *Zizyphus* | 4 | 4 | 8 |
| Control | 26 | 16 | 40 |

Biofilm Inhibition Assays—*P. gingivalis*+*F. nucleatum* in Rich Media

| Material | Biofilm formation/bacteria/ml |
|---|---|
| 1500 μg/ml *Zizyphus* | $3.5\times10^8$ |
| control | $5.3\times10^8$ |

*Zizyphus* 1500 μg/ml showed reduction in the biofilm formation compared to no inhibitor Biofilm Inhibition Assays in Defined Media

| Material | Crystal Violet Stain A590 of *P. gingivalis* biofilm |
|---|---|
| 1500 μg/ml *Zizyphus* | 0.18 |
| Control | 0.53 |

N.B. in a rich medium there was no obvious effect on the *P. gingivalis* biofilm using Crystal Violet Stain Discussion Compound 1 (Example 3) and the *Zizyphus* extract with 1% 4-hydroxymethyl-N-methyl-L-prolines 1-3 inhibited the sialidase of *Tannerella forsythia. Zizyphus* extract did not appear to have a directly antimicrobial effect but despite having a high sugar content may inhibit biofilm formation through prevention of nutrient acquisition, or limiting attachment to serum coated surfaces. *P. gingivalis* biofilm formation in TSB was not significantly inhibited by the plant extract but was inhibited when cultured in defined media (where serum-FBS is the only carbon and nitrogen source).

This suggests the extract containing the Compounds 1-3 was preventing nutrient acquisition by *P. gingivalis* through inhibition of its sialidase and possibly other enzymes, which could limit *P. gingivalis* protein catabolism. This would be particularly detrimental to nutrient acquisition from serum, and less so for nutrient acquisition from TSB, where the protein source (soybean meal) has already undergone enzymatic digestion. Arguably, the defined media is more representative of the situation in vivo, where *P. gingivalis* acquires nutrients by catabolism of host glycoproteins in the gingival crevicular fluid (GCF, similar in composition to serum), and other glycoproteins in blood and saliva.

*T. forsythia* is more fastidious than *P. gingivalis*, and efforts to culture it as a single species biofilm using the defined media have so far been unsuccessful. However, it could form biofilms on serum-coated surfaces in TSB. In this set of experiment *Zizyphus* extract appeared to inhibit *T. forsythia* biofilm formation.

These findings also indicate that the compounds of the invention may find application in various therapeutic treatments based on the inhibition of other bacterial sialidases, including *Gardnerella vaginalis*, a species associated with bacterial vaginosis and pre-term birth.

Example 6: *Zizyphus jujuba* Fruit 50% an. Ethanol Extract Mouse Studies

*Zizyphus jujuba* fruit extract was prepared in 50% aq ethanol and dried. Analysis by gas chromatography-mass spectroscopy (GCMS) of the extract showed high monosaccharide sugar content (>5%) and the presence of compounds 1-3 at 1%. The previous study on extract of *Z. spina-christi* extract was conducted on male ddy mice in maltose- and sucrose-loading tests (Example 2).

In this study, male C57BL/6J mice were used for glucose-, maltose- and sucrose-loading tests.

Methods

The animal experimental protocols were approved by the Animal Experiments Committee of the University of Toyama. The animals were fasted overnight. Glucose (2.5 g/kg body weight) or sucrose (2.5 g/kg body weight) as well as the extract were dissolved in 0.9% NaCl solution and administered to mice via a stomach tube. A control group was loaded with saline only. Blood samples for glucose measurements were obtained from the tail vein at 0, 15, 30, 60 and 120 min after sugar-loading. The blood glucose levels were measured by a portable kit. Antsence II™ (Sankyo Co. Ltd. Tokyo, Japan). The tests were as shown below.

- glucose-loading test 1000 mg/kg body weight (FIG. 2, Table 1)
- glucose-loading test 500 mg/kg body weight (FIG. 3, Table 2)
- sucrose-loading test 1000 mg/kg body weight (FIG. 4. Table 3)
- maltose-loading test 500 mg/kg body weight (FIG. 5, Table 4)

Results

FIG. 2 shows the effects of *Zizyphus* extract on blood glucose levels. Blood glucose concentrations of male C57BL/6J mouse after an oral load with 2.5 g/kg body weight glucose with *Zizyphus* extract (each 1000 mg/kg body weight) extracts (open circle). The control group was loaded with saline (closed circle). Each value represents the mean±SEM (n=5).

FIG. 3 shows the effects of *Zizyphus* extract on blood glucose levels. Blood glucose concentrations of male C57BL/6J mouse after an oral load with 2.5 g/kg body weight glucose with *Zizyphus* extract (each 500 mg/kg body weight) extracts (open circle). The control group was loaded with saline (closed circle). Each value represents the mean±SEM (n=5).

FIG. 4 shows the effects of *Zizyphus* extract on blood glucose levels. Blood glucose concentrations of male C57BL/6J mouse after an oral load with 2.5 g/kg body weight sucrose with *Zizyphus* extract (each 1000 mg/kg body weight) extracts (open circle). The control group was loaded with saline (closed circle). Each value represents the mean±SEM (n=5).

FIG. 5 shows the effects of *Zizyphus* extract on blood glucose levels. Blood glucose concentrations of male C57BL/6J mouse after an oral load with 2.5 g/kg body weight maltose with *Zizyphus* extract (each 500 mg/kg body weight) extracts (open circle). The control group was loaded with saline (closed circle). Each value represents the mean±SEM (n=5).

TABLE 1

Effects of *Zizyphus* extracts on blood glucose levels. (glucose-loading test)

| | mouse No. | 0 min | 15 min | 30 min | 60 min | 120 min |
|---|---|---|---|---|---|---|
| control | 1 | 120 | 323 | 178 | 133 | 90 |
| | 2 | 91 | 276 | 208 | 135 | 103 |
| | 3 | 129 | 240 | 207 | 138 | 117 |
| | 4 | 111 | 248 | 145 | 107 | 100 |
| | 5 | 118 | 285 | 183 | 117 | 87 |
| *Zizyphus* (each 1000 mg/WT) | 1 | 90 | 271 | 251 | 138 | 121 |
| | 2 | 98 | 315 | 230 | 176 | 121 |
| | 3 | 82 | 264 | 196 | 138 | 95 |
| | 4 | 117 | 307 | 191 | 138 | 126 |
| | 5 | 91 | 259 | 182 | 125 | 109 |

TABLE 2

Effects of *Zizyphus* extracts on blood glucose levels. (glucose-loading test)

| | mouse No. | 0 min | 15 min | 30 min | 60 min | 120 min |
|---|---|---|---|---|---|---|
| control | 1 | 120 | 323 | 178 | 133 | 90 |
| | 2 | 91 | 276 | 208 | 135 | 103 |
| | 3 | 129 | 240 | 207 | 138 | 117 |
| | 4 | 111 | 248 | 145 | 107 | 100 |
| | 5 | 118 | 285 | 183 | 117 | 87 |
| *Zizyphus* (each 500 mg/WT) | 1 | 90 | 271 | 251 | 138 | 121 |
| | 2 | 98 | 315 | 230 | 176 | 121 |
| | 3 | 82 | 264 | 196 | 138 | 95 |
| | 4 | 117 | 307 | 191 | 138 | 126 |
| | 5 | 91 | 259 | 182 | 125 | 109 |

TABLE 3

| Effects of *Zizyphus* extracts on blood glucose levels. (sucurose-loading test) | | | | | | |
|---|---|---|---|---|---|---|
| | mouse No. | 0 min | 15 min | 30 min | 60 min | 120 min |
| control | 1 | 61 | 168 | 216 | 169 | 84 |
| | 2 | 83 | 213 | 208 | 155 | 126 |
| | 3 | 76 | 226 | 227 | 175 | 105 |
| | 4 | 85 | 209 | 246 | 223 | 127 |
| | 5 | 75 | 256 | 240 | 187 | 109 |
| *Zizyphus* | 1 | 64 | 263 | 278 | 140 | 80 |
| (each 1000 | 2 | 80 | 230 | 238 | 172 | 100 |
| mg/WT) | 3 | 70 | 246 | 209 | 144 | 100 |
| | 4 | 75 | 251 | 222 | 136 | 105 |
| | 5 | 79 | 255 | 252 | 158 | 106 |

TABLE 4

| Effects of *Zizyphus* extracts on blood glucose levels. (maltose-loading test) | | | | | | |
|---|---|---|---|---|---|---|
| | mouse No. | 0 min | 15 min | 30 min | 60 min | 120 min |
| control | 1 | 58 | 345 | 270 | 204 | 122 |
| | 2 | 80 | 291 | 275 | 151 | 115 |
| | 3 | 74 | 357 | 284 | 182 | 124 |
| | 4 | 109 | 337 | 246 | 173 | 111 |
| | 5 | 85 | 295 | 206 | 172 | 106 |
| *Zizyphus* | 1 | 68 | 293 | 339 | 204 | 143 |
| (each 500 | 2 | 87 | 302 | 254 | 148 | 93 |
| mg/WT) | 3 | 77 | 357 | 369 | 182 | 104 |
| | 4 | 67 | 309 | 382 | 193 | 122 |
| | 5 | 63 | 264 | 319 | 237 | 116 |

Conclusion

The *Zizyphus jujuba* fruit extract which contained additional monosaccharides suppressed blood glucose in both glucose and sucrose challenge tests. The effects on the maltose- or sucrose-loading conditions could have been produced by maltase or sucrase inhibition except that the extract showed no significant glucosidase inhibition. The glucose-loading test results suggest a different mechanism independent of glucosidase inhibition and perhaps an effect on insulin release or other mechanisms.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of treating bacterial or viral infection comprising administering an effective amount of a composition comprising an isolated 4-hydroxymethyl-proline selected from:

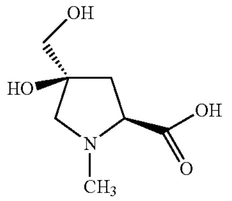

3

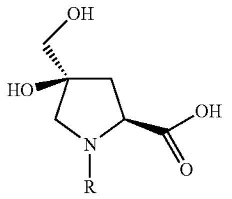

3b

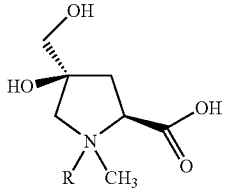

3c

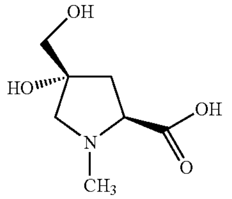

4

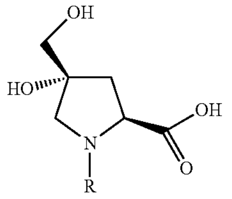

4b

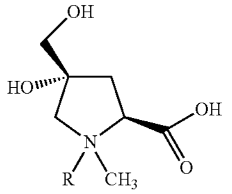

4c or a pharmaceutically acceptable salt or derivative thereof, in which R represents optionally substituted C1-6 alkyl, C1-6 alkenyl or C1-6 alkynyl, to a subject.

2. The method of claim 1 wherein the 4-hydroxymethyl-proline is selected from:

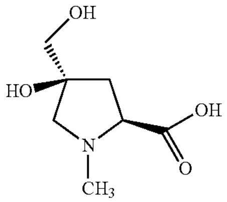

3

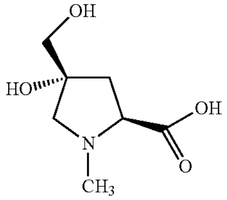

4 or a pharmaceutically acceptable salt or derivative thereof.

3. The method of claim 1 wherein the isolated 4-hydroxymethyl-proline is synthetic or is purified from a botanical source selected from: (a) plants of the genus *Zizyphus*; and (b) plants of the genus *Paullinia*, optionally wherein the botanical source: (i) is selected from a plant species selected from: *Z. jujuba, Z. spina-christi, Z. lotus, Z. mauritiana, Z. joazeiro*, and *Paullinia cupana*; and/or (ii) comprises fruit, fruit parts, fruit extracts, fruit juices, seeds, bark, roots and/or leaves.

4. The method of claim 1 wherein the composition further comprises a pharmaceutically acceptable excipient, and/or is (a) in the form of a pharmaceutical pack, kit or patient pack; or (b) in unit dosage form.

5. The method of claim 1 wherein treating bacterial or viral infection comprises:

(i) inhibiting commensal and/or pathogenic bacterial growth in vivo; or (ii) disrupting host-bacterial cell interactions, and/or inhibiting or eliminating bacterial biofilm formation in a mammalian host.

6. The method of claim 1, wherein the isolated 4-hydroxymethyl-proline is present in the composition at a level of at least: 0.5%, 1% w/w, 5% w/w, 10% w/w; 15% w/w; 20% w/w; 25% w/w; 30% w/w; 35% w/w; 40% w/w; 45% w/w; 50% w/w, 60% w/w, 70% w/w, 80% w/w, 90% w/w, 99% w/w on a dry weight basis.

7. A process for the production of the composition of claim 1, said process comprising the steps of:

(a) providing plant material from a botanical source;

(b) extracting 4-hydroxymethyl-proline as defined in claim 1 from said plant material; and then (c) formulating said extracted 4-hydroxymethyl-proline with a pharmaceutically-acceptable excipient to produce a pharmaceutical composition.

8. A process for producing a pharmaceutical composition, herbal medicine or nutraceutical comprising the step of monitoring the quality of said pharmaceutical composition, herbal medicine or nutraceutical by detecting the presence or absence or measuring the amount of a 4-hydroxymethyl-proline as defined in claim 1 in a sample of said pharmaceutical composition, herbal medicine or nutraceutical.

* * * * *